US008906964B2

(12) United States Patent
Bobotas et al.

(10) Patent No.: US 8,906,964 B2
(45) Date of Patent: Dec. 9, 2014

(54) METHODS OF ADMINISTERING COMPOSITIONS COMPRISING DOCOSAPENTAENOIC ACID

(71) Applicant: Matinas BioPharma, Inc., Bedminster, NJ (US)

(72) Inventors: George Bobotas, Tarpon Springs, FL (US); Abdel Aziz Fawzy, Boynton Beach, FL (US)

(73) Assignee: Matinas BioPharma, Inc., Bedminster, NJ (US)

( * ) Notice: Subject to any disclaimer, the term of this patent is extended or adjusted under 35 U.S.C. 154(b) by 0 days.

(21) Appl. No.: 14/101,165

(22) Filed: Dec. 9, 2013

(65) Prior Publication Data

US 2014/0100273 A1    Apr. 10, 2014

Related U.S. Application Data

(63) Continuation-in-part of application No. PCT/US2013/046176, filed on Jun. 17, 2013.

(60) Provisional application No. 61/780,948, filed on Mar. 13, 2013, provisional application No. 61/734,331, filed on Dec. 6, 2012, provisional application No. 61/660,757, filed on Jun. 17, 2012.

(51) Int. Cl.
*A61K 31/20* (2006.01)
*A61K 31/201* (2006.01)
*A61K 31/202* (2006.01)
*A61K 31/40* (2006.01)
*A61K 31/232* (2006.01)

(52) U.S. Cl.
CPC ............. *A61K 31/201* (2013.01); *A61K 31/202* (2013.01); *A61K 31/40* (2013.01); *A61K 31/232* (2013.01); *Y10S 514/893* (2013.01)
USPC ........................................ 514/558; 514/893

(58) Field of Classification Search
USPC ................................................ 514/558, 893
See application file for complete search history.

(56) References Cited

U.S. PATENT DOCUMENTS

| | | |
|---|---|---|
| 5,656,667 A | 8/1997 | Breivik |
| 5,698,594 A | 12/1997 | Breivik et al. |
| 5,886,037 A | 3/1999 | Klor et al. |
| 6,245,811 B1 | 6/2001 | Horrobin et al. |
| 6,479,544 B1 | 11/2002 | Horrobin |
| 7,498,359 B2 | 3/2009 | Yokoyama et al. |
| 7,795,308 B2 | 9/2010 | Yokoyama et al. |
| 8,198,324 B2 | 6/2012 | Fortin |
| 8,258,183 B2 | 9/2012 | Yokoyama et al. |
| 8,367,725 B2 | 2/2013 | Yokoyama et al. |
| 8,399,516 B2 | 3/2013 | Bryhn et al. |
| 8,461,141 B2 | 6/2013 | Hashizume |
| 8,609,138 B2 | 12/2013 | Fujii et al. |
| 8,618,168 B2 | 12/2013 | Fujii et al. |
| 2002/0016312 A1 | 2/2002 | Seed et al. |
| 2003/0199481 A1* | 10/2003 | Garavani et al. ............... 514/165 |
| 2006/0188529 A1 | 8/2006 | Bobotas et al. |
| 2006/0211749 A1 | 9/2006 | Bobotas et al. |
| 2006/0211762 A1 | 9/2006 | Rongen et al. |
| 2006/0211763 A1 | 9/2006 | Fawzy et al. |
| 2006/0241088 A1 | 10/2006 | Arterburn et al. |
| 2007/0021504 A1 | 1/2007 | Yokoyama et al. |
| 2007/0036862 A1 | 2/2007 | Rongen et al. |
| 2007/0098787 A1 | 5/2007 | Kakiuchi |
| 2007/0104779 A1 | 5/2007 | Rongen et al. |
| 2007/0104856 A1 | 5/2007 | Standal et al. |
| 2007/0185198 A1 | 8/2007 | Yokoyama et al. |
| 2007/0191467 A1 | 8/2007 | Rongen et al. |
| 2007/0196465 A1 | 8/2007 | Bobotas et al. |
| 2007/0265340 A1 | 11/2007 | Shalwitz et al. |
| 2008/0085911 A1 | 4/2008 | Rongen et al. |
| 2008/0113046 A1 | 5/2008 | Gardette |
| 2008/0200707 A1 | 8/2008 | Shimano et al. |
| 2008/0269330 A1 | 10/2008 | Stahl et al. |
| 2009/0054329 A1 | 2/2009 | Willemsen et al. |
| 2009/0105340 A1 | 4/2009 | Yokoyama et al. |
| 2009/0182022 A1 | 7/2009 | Rongen et al. |
| 2009/0203778 A1 | 8/2009 | Bryhn et al. |
| 2009/0239927 A1 | 9/2009 | Bobotas |
| 2010/0010026 A1 | 1/2010 | Rongen et al. |
| 2010/0021573 A1 | 1/2010 | Gonzalez et al. |
| 2010/0069492 A1 | 3/2010 | Geiringen et al. |
| 2011/0034555 A1 | 2/2011 | Osterloh et al. |
| 2011/0071090 A1 | 3/2011 | Driscoll |

(Continued)

FOREIGN PATENT DOCUMENTS

| | | |
|---|---|---|
| CN | 102755350 A * | 10/2012 |
| GB | 0301701.9 | 2/2004 |

(Continued)

OTHER PUBLICATIONS

Bio-Sources, Omega-3 with EPA-DHA-DPA, Dec. 18, 2008, printed from http://web.archive.org/web/20081218175343/http://www.bio-sources.com/omega3, 3 pages.*
Gotoh et al. Effects of three different highly purified n-3 series highly unsaturated fatty acids on lipid metabolism in C57BL/KsJ-db/db Mice, Journal of Agricultural and Food Chemistry (2009) 57:11047-11054.
Kaur et al. "Docosapentaenoic acid (22:5n-3) down-regulates the expression of genes involved in faty synthesis in liver cells" Prostaglandins, Leukotrienes, and Essential Fatty Acids (2011)85:155-161.
Kaur et al. "Docosapentaenoic acid (22:5n-3): A review of its biological effects" Progress in Lipid Research, (2011) 50:28-34.
Kaur et al. "Orally administered [14C] DPA and [14C} DHA are metabolized differently to [14C] EPA in rats" British Journal of Nutrition (2013) 109(3): 441-448.

(Continued)

*Primary Examiner* — Gigi Huang
(74) *Attorney, Agent, or Firm* — Arent Fox, LLP

(57) ABSTRACT

The present invention relates to compositions comprising docosapentaenoic acid and methods of reducing lipid parameters, such as triglycerides, total cholesterol, low density lipoprotein (LDL) cholesterol, non-HDL cholesterol, free fatty acids, and other lipids, comprising administration of omega-3 docosapentaenoic acid.

21 Claims, 3 Drawing Sheets

(56) References Cited

U.S. PATENT DOCUMENTS

| | | |
|---|---|---|
| 2011/0118350 A1 | 5/2011 | Yokoyama et al. |
| 2011/0160161 A1 | 6/2011 | Sampalis |
| 2011/0177061 A1 | 7/2011 | Aisen et al. |
| 2011/0178105 A1 | 7/2011 | Gillies |
| 2011/0218243 A1* | 9/2011 | Rowe .......................... 514/549 |
| 2012/0035262 A1 | 2/2012 | Osterloh et al. |
| 2012/0093922 A1 | 4/2012 | Manku et al. |
| 2012/0100123 A1 | 4/2012 | Gonzalez et al. |
| 2012/0100223 A1 | 4/2012 | Bhagat |
| 2012/0232141 A1 | 9/2012 | Husvedt et al. |
| 2012/0237594 A1 | 9/2012 | Manku et al. |
| 2012/0251582 A1 | 10/2012 | Fortin |
| 2012/0264824 A1 | 10/2012 | Mizuguchi et al. |
| 2012/0302639 A1 | 11/2012 | Jackowski |
| 2013/0045193 A1 | 2/2013 | Gonzalez et al. |
| 2013/0059768 A1 | 3/2013 | Hallaraker et al. |
| 2013/0065956 A1 | 3/2013 | Yokoyama et al. |
| 2013/0079310 A1 | 3/2013 | Jackowski et al. |
| 2013/0095179 A1 | 4/2013 | Davidson et al. |
| 2013/0115284 A1 | 5/2013 | Fujii et al. |
| 2013/0177643 A1 | 7/2013 | Maines et al. |
| 2013/0209556 A1 | 8/2013 | Maines et al. |

FOREIGN PATENT DOCUMENTS

| | | |
|---|---|---|
| WO | WO 2004/064716 | 8/2004 |
| WO | WO 2006/062748 | 5/2007 |
| WO | WO 2008/115529 | 9/2008 |
| WO | WO 2010/103402 | 9/2010 |
| WO | WO 2010/147994 | 12/2010 |
| WO | WO 2011060492 A1 * | 5/2011 |
| WO | WO 2011/092467 | 8/2011 |
| WO | WO 2011/109724 | 9/2011 |
| WO | WO 2012/112531 | 8/2012 |
| ZA | 93/6133 | 3/1994 |

OTHER PUBLICATIONS

Kaur et al. "Short-term docosapentaenoic acid (22:5n-3) supplementation increases tissue docosapentaenoic acid, DHA and EPA concentrations in rats" British Journal of Nutrition (2010) 103:32-37.

Kaur, "Docosapentaenoic acid: its metabolism and effect on lipogenic gene expression" Deakin University, Aug. 2010.

Kelly et al. "The polyunsaturated fatty acids, EPA and DPA exert a protective effect in the hippocampus of the aged rat" Neurobiology of Aging (2011) 32:2318.e1-2318.e15.

Linderborg et al. "Postprandial metabolism of docosapentaenoic acid (DPA, 22:5n-3) and eicosapentaenoic acid (EPA, 20:5n-3) in humans" Prostaglandins, Leukotrienes, and Essential Fatty Acids, (2013) 88:313-319.

Mann et al. "Effects of seal oil and tuna-fish oil on platelet parameters and plasma lipid levels in healthy subjects" Lipids, (2010) 45:669-681.

Meyer er al. "Comparison of seal oil to tuna oil on plasma lipid levels and blood pressure in hypertriglyceridaemic subjects" Lipids, (2009) 44:827-835.

Mozaffarian et al. "(n-3) Fatty acids and cardiovascular health: Are effects of EPA and DHA shared or complementary?" The Journal of Nutrition, (2012), 142:614S-625S.

Larsen et al. Heneicosapentaenoate (21:5n-3): its incorporation into lipids and its effect on arachidonic acid and eicosanoid synthesis, Lipids, Jul. 1997, 32(7): 707-14.

* cited by examiner

Fasting Plasma Lipid Values After Seven (7) Days of Dosing absolute plasma values, average for each group

| Group | Dose | n | TGs | Chol | HDL | LDL | FFA | non-HDL C |
|---|---|---|---|---|---|---|---|---|
| Vehicle | Corn Oil | 16 | 439 | 231 | 75 | 22 | 1.80 | 156 |
| DPA | 50 mg/kg | 8 | 204 | 212 | 69 | 13 | 1.49 | 143 |
| DPA | 200 mg/kg | 8 | 301 | 218 | 72 | 13 | 1.61 | 146 |
| DPA | 400 mg/kg | 8 | 387 | 230 | 77 | 13 | 1.68 | 153 |
| DPA | 1000 mg/kg | 8 | 341 | 242 | 78 | 15 | 1.51 | 164 |

% difference from vehicle

| Group | Dose | n | TGs | Chol | HDL | LDL | FFA | non-HDL C |
|---|---|---|---|---|---|---|---|---|
| DPA | 50 mg/kg | 8 | -54% | -8% | -8% | -40% | -17% | -8% |
| DPA | 200 mg/kg | 8 | -31% | -5% | -3% | -42% | -10% | -6% |
| DPA | 400 mg/kg | 8 | -12% | 0% | 3% | -40% | -7% | -2% |
| DPA | 1000 mg/kg | 8 | -22% | 5% | 4% | -31% | -16% | 5% |

| | | | |
|---|---|---|---|
| TG | triglycerides (mg/dL) | LDL | low density lipoprotein (mg/dL) |
| Chol | cholesterol (mg/dL) | FFA | free fatty acids (mmol) |
| HDL | high density lipoprotein (mg/dL) | non-HDL = | Chol − HDL (mg/dL) |

FIG. 1

METHODS OF ADMINISTERING COMPOSITIONS COMPRISING DOCOSAPENTAENOIC ACID

RELATED APPLICATIONS

This application is a continuation-in-part (CIP) application of PCT International Application No. PCT/US13/46176, filed on Jun. 17, 2013, which claims the benefit of U.S. Provisional Patent Application No. 61/660,757, filed Jun. 17, 2012, U.S. Provisional Patent Application No. 61/734,331, filed Dec. 6, 2012, and U.S. Provisional Patent Application No. 61/780,948, filed Mar. 13, 2013, the contents of which are incorporated herein by reference.

FIELD OF INVENTION

The present invention relates to a method comprising administration of docosapentaenoic acid compositions for the reduction of lipid parameters, such as triglycerides, total cholesterol, low density lipoprotein (LDL) cholesterol, non-HDL cholesterol, free fatty acids, and other lipids. The present invention also relates to a method comprising administration of docosapentaenoic acid compositions for the increase of high density lipoprotein (HDL) cholesterol. The methods of the present invention may be useful for the treatment of a condition selected from the group consisting of: hypertriglyceridemia; hypercholesterolemia; mixed dyslipidemia; coronary heart disease (CHD); vascular disease; cardiovascular disease; acute coronary syndrome; atherosclerotic disease and related conditions; heart failure; cardiac arrhythmias; coagulatory conditions associated with cardiac arrhythmias; ischemic dementia; vascular dementia; hypertension; coagulation related disorders; nephropathy; kidney or urinary tract disease; retinopathy; cognitive and other CNS disorders; autoimmune diseases; inflammatory diseases; asthma or other respiratory disease; dermatological disease; metabolic syndrome; diabetes, diabetes mellitus or other form of metabolic disease; liver disease; non-alcoholic fatty liver disease; disease of the gastrointestinal tract; disease of the male or female reproductive system or related secondary sexual organs; a cancer of any type, including lymphomas and myelomas; an infection caused by a virus, bacterium, fungus, protozoa or other organism; and the treatment and/or prevention and/or reduction of cardiac events and/or cardiovascular events and/or vascular events and/or symptoms. The present invention also relates to treatment of such conditions in with concomitant treatments regimes or combination products with other active pharmaceutical ingredients.

BACKGROUND OF THE INVENTION

In humans, cholesterol and triglycerides are part of lipoprotein complexes in the bloodstream, and can be separated via ultracentrifugation into high-density lipoprotein (HDL), intermediate-density lipoprotein (IDL), low-density lipoprotein (LDL) and very-low-density lipoprotein (VLDL) fractions. Cholesterol and triglycerides are synthesized in the liver, incorporated into VLDL, and released into the plasma. High levels of total cholesterol (total-C), LDL-cholesterol, and apolipoprotein B (a membrane complex for LDL-cholesterol and VLDL-cholesterol, as well as IDL-cholesterol in rare individuals suffering from a disorder resulting in significant IDL-cholesterol levels) promote human atherosclerosis; these elevated levels are often referred to as hypercholesterolemia. Decreased levels of HDL-cholesterol and its transport complex, apolipoprotein A, as well as elevated levels of apolipoprotein C-III and serum triglycerides (TG) are also associated with the development of atherosclerosis. Further, cardiovascular morbidity and mortality in humans can vary directly with the level of total-C, LDL-cholesterol and TG and inversely with the level of HDL-cholesterol. In addition, researchers have found that non-HDL-cholesterol is an important indicator of hypertriglyceridemia (elevated triglycerides), vascular disease, atherosclerotic disease and related conditions. Therefore, non-HDL-cholesterol and fasting TG reduction has also been specified as a treatment objective in NCEP ATP III. Fasting TG is commonly used as a key measure for TG in lipid management, because it minimizes the confounding factor of TG recently absorbed from meals, including the high variability of the content of meals and high variability of post-meal (post-prandial) spikes in TG. In some preferred embodiments, we refer to fasting TG levels when we refer to triglycerides or TG.

The NCEP ATPIII treatment guidelines identify HMG-CoA reductase inhibitors ("statins") as the primary treatment option for hypercholesterolemia. In patients with TG<500 mg/dL, LDL-cholesterol is the primary treatment parameter. Many patients, however, have increased LDL-cholesterol combined with high TG and low HDL-cholesterol, a condition also known as mixed dyslipidemia. Patients with hypercholesteremia or mixed dyslipidemia often present with high blood levels of LDL-cholesterol (i.e. greater than 190 mg/dl) and TG (i.e. levels of 200 mg/dl or higher). The use of diet and single-drug therapy does not always decrease LDL-cholesterol and TG adequately enough to reach targeted values in patients with mixed dyslipidemia with or without a concomitant increase in triglycerides. In these patients, a combined therapy regimen of a statin and a second anti-dyslipidemic agent is often desired. This second agent has historically been a fibrate (i.e. gemfibrozil, bezafibrate, or fenofibrate) or extended release niacin. Over the few years, the use omega-3 fatty acid concentrates in combination with a statin has been growing rapidly due to concerns about the lack of outcome benefits with fibrates (i.e. the FIELD study) or extended release niacin (i.e. the AIM-HIGH study). In patients with isolated hypertriglyceridemia, the use of omega-3 fatty acid concentrates has also grown versus fibrates and extended release niacin.

Marine oils, also commonly referred to as fish oils, are a good source of the two main omega-3 fatty acids, eicosapentaenoic acid (EPA) and docosahexaenoic acid (DHA), which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides (TG), increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects.

The table directly below lists the most common omega-3 fatty acids, including their 3-letter abbreviation code. In this application, the use of any of the 3-letter abbreviations shall refer to the omega-3 fatty acid, unless otherwise indicated (e.g. DPA or DPA 22:5 (n-3) or DPA 22:5-n3 or DPA 22:5n3 or DPA-n3, which all refer to the omega-3 isomer of docosapentaenoic acid).

| Common Name for Omega-3 Fatty Acid (+abbreviation) | Codified Lipid Name | Chemical Name |
|---|---|---|
| Hexadecatrienoic acid (HTA) | 16:3 (n-3) | all-cis-7,10,13-hexadecatrienoic acid |
| α-Linolenic acid (ALA) | 18:3 (n-3) | all-cis-9,12,15-octadecatrienoic acid |
| Stearidonic acid (SDA) | 18:4 (n-3) | all-cis-6,9,12,15-octadecatetraenoic acid |
| Eicosatrienoic acid (ETE) | 20:3 (n-3) | all-cis-11,14,17-eicosatrienoic acid |
| Eicosatetraenoic acid (ETA) | 20:4 (n-3) | all-cis-8,11,14,17-eicosatetraenoic acid |
| Eicosapentaenoic acid (EPA) | 20:5 (n-3) | all-cis-5,8,11,14,17-eicosapentaenoic acid |
| Heneicosapentaenoic acid (HPA) | 21:5 (n-3) | all-cis-6,9,12,15,18-heneicosapentaenoic acid |
| Docosapentaenoic acid (DPA) or Clupanodonic acid | 22:5 (n-3) | all-cis-7,10,13,16,19-docosapentaenoic acid |
| Docosahexaenoic acid (DHA) | 22:6 (n-3) | all-cis-4,7,10,13,16,19-docosahexaenoic acid |
| Tetracosapentaenoic acid (TPA) | 24:5 (n-3) | all-cis-9,12,15,18,21-tetracosapentaenoic acid |
| Tetracosahexaenoic acid (THA) or Nisinic acid | 24:6 (n-3) | all-cis-6,9,12,15,18,21-tetracosahexaenoic acid |

One form of omega-3 fatty acids is a concentrate of omega-3, long chain, polyunsaturated fatty acids from fish oil containing DHA ethyl esters, EPA ethyl esters as well as ethyl esters of other omega-3 fatty acids (described in USP35 for LOVAZA®) and is sold under the trademarks OMACOR® and LOVAZA®. Such a form of omega-3 fatty acid comprises at least 90% omega-3 fatty acids of which at least 80% EPA+DHA (in a ratio of 1.2:1) and is described, for example, in U.S. Pat. Nos. 5,502,077, 5,656,667 and 5,698,594. LOVAZA® (omega-3-acid ethyl esters) is indicated for the treatment of patients with hypertriglyceridemia with TG levels of 500 mg/dL or higher.

Another form of omega-3 fatty acid concentrate is sold under the trademark EPADEL® for the treatment of dyslipidemia. This product is described as 98% EPA ethyl ester in Lancet (Vol. 369; Mar. 31, 2007; 1090-1098) reporting on a large outcome study with EPADEL®. EPADEL® is known to contain less than 1% of any fatty acid other than EPA.

Similar to EPADEL®, another form of omega-3 fatty acid concentrate also consists almost entirely of EPA ethyl ester and is known under its developmental stage name AMR101 or its trade name VASCEPA®. This product is described in US patent application 2010/0278879 as comprising at least 95% EPA (typically referred to as 97% or at least 96% in company releases and references) and less than 1% of any other fatty acid. AMR101 was previously under development for the treatment of Huntingdon's Disease but failed in phase III clinical development. Subsequently, AMR101 was entered in a development program for hypertriglyceridemia and mixed dyslipidemia.

Yet another concentrate of omega-3, long chain, polyunsaturated fatty acids from fish oil containing approximately 75% DHA and EPA as free fatty acids is known under its developmental stage name EPANOVA™. This product is described as comprising approximately 55% EPA and 20% DHA. EPANOVA™ was previously under development for the treatment of Crohn's Disease but failed in phase III clinical development. Subsequently, EPANOVA™ was entered in a development program for hypertriglyceridemia and mixed dyslipidemia.

Generally, the bioavailability and therapeutic effect of omega-3 fatty acid compositions is dose dependent, i.e., the higher the dose, the greater the therapeutic affect and bioavailability. However, the effect of each specific omega-3 fatty acid composition may be different, and therefore the level of therapeutic effect of one composition at a given dose cannot necessarily be inferred from the level of therapeutic effects of other omega-3 fatty acid compositions at the same or similar dose.

For instance, in the MARINE study, it was found that four 1-gram capsules of AMR101/VASCEPA® significantly reduced fasting TG in patients with very high triglycerides (TG>500 mg/dL) (March 2011, ACC poster reporting top-line results of the MARINE study), similar to four 1-gram capsules of LOVAZA® but in a less potent manner (LOVAZA® prescribing information, December 2010). In this same study, AMR101 slightly and non-significantly changed LDL-C while LOVAZA® shows a large significant increase in this same population, putting the latter at a disadvantage. Table A directly below compares these profiles.

TABLE A

Comparison of therapeutic profile of Lovaza and Vascepa in patients with very high triglycerides (>500 mg/dL)

| | LOVAZA - 4 gram/day | | Vascepa - 4 gram/day | | Vascepa - 2 gram/day | |
|---|---|---|---|---|---|---|
| | % change vs. Placebo | p-value | % change vs. Placebo | p-value | % change vs. Placebo | p-value |
| TG | −51.6 | p < 0.05 | −33.1 | p < 0.05 | −19.7 | p < 0.05 |
| Total-C | −8.0 | p < 0.05 | −16.3 | p < 0.0001 | −6.8 | p = 0.0148 |
| LDL-C | 49.3 | p < 0.05 | −2.3 | NS | 5.2 | NS |
| VLDL-C | −40.8 | p < 0.05 | −28.6 | p = 0.0002 | −15.3 | p = .038 |
| Non-HDL-C | −10.2 | p < 0.05 | −17.7 | p < 0.0001 | −8.1 | p = .0182 |
| Apo-B | NR | | −8.5 | p = 0.0019 | −2.6 | NS |
| HDL-C | 9.1 | p < 0.05 | −3.6 | NS | 1.5 | NS |

NR = Not Reported;
NS = Not Significant

In another study with AMR101/VASCEPA®, the ANCHOR study, it was found that four 1-gram capsules of AMR101 significantly reduced fasting TG in patients on statin therapy with high triglycerides (TG 200-499 mg/dL), similar to four 1-gram capsules of LOVAZA® but in a less potent manner (Study in table 3, LOVAZA® prescribing information, December 2010). In this same study, AMR101 decreased LDL-C at 4 gr/day while LOVAZA® shows a significant LDL-C increase in this same population. AMR101 is also more potent than LOVAZA® in reducing non-HDL-cholesterol in this population. Table B directly below compares these profiles.

TABLE B

Therapeutic profile comparison of Lovaza and Vascepa
in patients on statin with high triglycerides (TG 200-499 mg/dL)

|  | LOVAZA - 4 gram/day | | Vascepa - 4 gram/day | | Vascepa - 2 gram/day | |
| --- | --- | --- | --- | --- | --- | --- |
|  | % change vs. Placebo | p-value | % change vs. Placebo | p-value | % change vs. Placebo | p-value |
| TG | −23.2 | p < 0.0001 | −21.5 | p < 0.0001 | −10.1 | p = 0.0005 |
| Total-C | −3.1 | p < 0.05 | NR | p < 0.0001 | NR | p = 0.0019 |
| LDL-C | 3.5 | p = 0.05 | −6.3 | p = 0.0067 | −3.6 | NS |
| VLDL-C | −20.3 | p < 0.05 | −24.4 | p < 0.0001 | −10.5 | p = 0.0093 |
| Non-HDL-C | −6.8 | p < 0.0001 | −13.6 | p < 0.0001 | −5.5 | p = 0.0054 |
| Apo-B | −2.3 | p < 0.05 | −9.3 | p < 0.0001 | −3.8 | p = 0.0170 |
| HDL-C | 4.6 | p < 0.05 | −4.5 | p = 0.0013 | −2.2 | NS |

NS = Not Significant

The resulting lipid profile of AMR101 versus LOVAZA® in highly similar patient populations indicates that there are significant benefits of using an almost pure EPA oil composition as opposed to an omega-3 mixture as in LOVAZA®. These benefits translate into better non-HDL- and LDL-Cholesterol reduction with the pure EPA form, where these benefits are less or, in the case of the LDL-C effect, the opposite.

The recently released results from Omthera's EVOLVE trial with EPANOVA™, in patients with very high triglycerides (TG≥500 mg/dL), described a TG reduction of 31% versus baseline for the 4 gram per day dose and 26% versus baseline for the 2 gram per day dose, with 10% and 8% non-HDL reduction respectively. It appears that the TG-reducing potency of EPANOVA™ is similar to the potency of AMR101. No data were reported by Omthera on the LDL-C effect in the EVOLVE trial.

The recently released results from Omthera's ESPRIT trial with EPANOVA™, in patients with high triglycerides (TG 200-499 mg/dL) while on statin therapy, described a TG reduction of 21% versus baseline for the 4 gram per day dose and 15% versus baseline for the 2 gram per day dose, with 7% and 4% non-HDL reduction respectively. It appears that the TG-reducing potency of EPANOVA™ is similar to the potency of AMR101. No data were reported by Omthera on the LDL-C effect in the ESPRIT trial.

From the comparison of LOVAZA® versus AMR101 data, there appears to be a benefit of using pure EPA concentrates for dyslipidemia treatment over omega-3 mixtures with regard to LDL-Cholesterol and non-HDL-cholesterol effects. With the NCEP ATP III guidelines placing LDL-cholesterol and non-HDL-cholesterol reduction at the top of the treatment hierarchy for patients with TG<500 mg/dL, AMR101 is clearly superior to LOVAZA® in this patient category.

In another example, in the ECLIPSE Study, the bioavailability of EPANOVA™ is compared to LOVAZA® under high fat meal and low fat meal dosing conditions.

In the ECLIPSE study it is found that EPANOVA™ is significantly more bioavailable than LOVAZA® after single dose administration (four capsules of 1 gram for both products), both by Cmax (maximum concentration) and AUC (area under curve) measures (see Table C below, where Cmax and AUC are estimated from the data points in FIGS. 1 and 2). Relative to LOVAZA® under high fat meal conditions, EPANOVA™ is 1.17× more bioavailable by Cmax and 1.27 by AUC comparison. Under low fat meal conditions, LOVAZA® has only 15% AUC and 12% Cmax of the bioavailability versus LOVAZA® under high fat meal conditions, whereas EPANOVA™ under low fat meal conditions has 78% AUC and 53% Cmax of the bioavailability versus LOVAZA® under high fat meal conditions. EPANOVA™ under low fat meal conditions has 62% AUC and 46% Cmax of the bioavailability versus EPANOVA™ under high fat meal conditions.

TABLE C

Comparison of bioavailability of EPA + DHA in Plasma for Lovaza
(4 g) and Epanova (4 g) under high-fat and low-fat meal dosing conditions

|  | LOVAZA - High Fat | LOVAZA - Low Fat | Epanova - High Fat | Epanova - Low Fat |
| --- | --- | --- | --- | --- |
| Cmax EPA + DHA | 385 nmol/ml | 45 nmol/ml | 450 nmol/ml | 205 nmol/ml |
| Est. AUC, 0-24 EPA + DHA | 3080 nmol * hr/ml | 465 nmol * hr/ml | 3920 nmol * hr/ml | 2415 nmol * hr/ml |
| Tmax EPA + DHA | 5 hrs | 10 hrs | 5 hrs | 5 hrs |
| Multiple of Lovaza-HF AUC | 1.00× | 0.15× x | 1.27× | 0.78× |
| Multiple of LF vs. HF AUC | NA | 0.15 × Lovaza-HF AUC | NA× | 0.62 × Epanova-HF AUC |
| Multiple of Lovaza-HF Cmax | 1.00× | 0.12× | 1.17× | 0.53× |
| Multiple of LF vs. HF Cmax | NA | 0.12 × Lovaza-HF Cmax | NA× | 0.46 × Epanova-HF Cmax |
| Low fat meal - AUC vs. Lov. | NA | 1.00× | NA | 5.19× |
| Low fat meal - Cmax vs. Lov. | NA | 1.00× | NA | 4.56× |

TABLE C-continued

Comparison of bioavailability of EPA + DHA in Plasma for Lovaza
(4 g) and Epanova (4 g) under high-fat and low-fat meal dosing conditions

|  | LOVAZA - High Fat | LOVAZA - Low Fat | Epanova - High Fat | Epanova - Low Fat |
|---|---|---|---|---|
| High fat meal - AUC vs. Lov. | 1.00× | NA | 1.27× | NA |
| High fat meal - Cmax vs. Lov. | 1.00× | NA | 1.17× | NA |

Omega-3 fatty acids are known to be "essential fatty acids". There are two series of essential fatty acids (EFAs) in humans. They are termed "essential" because they cannot be synthesized de novo in mammals. These fatty acids can be interconverted within a series, but the omega-6 (n-6) series cannot be converted to the omega-3 series nor can the omega-3 (n-3) series be converted to the omega-6 series in humans. The main EFAs in the diet are linoleic acid of the omega-6 series and alpha-linolenic acid of the omega-3 series. However, to fulfill most of their biological effects these "parent" EFAs must be metabolised to the other longer chain fatty acids. Each fatty acid probably has a specific role in the body. The scientific literature suggests that particularly important in the n-6 series are dihomo-gammalinolenic acid (DGLA, 20:3-n6) and arachidonic acid (ARA, 20:4-n6), while particularly important in the n-3 series are eicosapentaenoic acid (EPA, 20:5-n3) and docosahexaenoic acid (DHA, 22:6-n3).

U.S. Pat. No. 6,479,544 describes an invention in which it is found that ARA is highly desirable rather than undesirable and it may be helpful to administer ARA in association with EPA. This invention provides pharmaceutical formulations containing eicosapentaenoic acid or any appropriate derivative (hereinafter collectively referred to as EPA) and arachidonic acid (ARA), as set out in the granted claims for this patent. ARA may be replaced by one or more of its precursors, DGLA or GLA. In this reference, the ratio of EPA to ARA is preferably between 1:1 and 20:1.

Patent application PCT/GB 2004/000242 describes the treatment or prevention of psoriasis with a formulation comprising more than 95% EPA and less than 2% DHA. In another embodiment of this invention the EPA is replaced with DPA.

Patent application PCT/NL 2006/050291 (WO/2007/058538, GB 0301701.9) describes combinations of indigestible oligosaccharides and long chain poly-unsaturated fatty acids such as ARA, EPA, DA, and combinations thereof to improve intestinal barrier integrity, improving barrier function, stimulating gut maturation and/or reducing intestinal barrier permeability.

Lindeborg et al. (*Prostag Leukotr Ess*, 2013, 88:313-319) discloses a study evaluating postprandial metabolism of docosapentaenoic acid (DPA) and eicosapentaenoic acid (EPA) in humans.

Holub et al. (*Lipids*, 2011, 46:399-407) discloses a study assessing the effect of oral supplementation with docosapentaenoic acid (DPA) on levels of serum and tissue lipid classes and their fatty acid compositions in rat liver, heart, and kidney Given the highly beneficial efficacy and side-effect profile of omega-3 fatty acid concentrates, these compositions are increasingly popular for the treatment of patients with dyslipidemias. However, with the increased popularity of omega-3 fatty acid concentrates, there is an unmet medical need for omega-3 fatty acid containing compositions with improved bioavailability and a more optimal ratio of potency in reducing TG versus the resulting cholesterol profile. Specifically, agents with both a higher potency than AMR101/ EPADEL® and lesser increase in LDL-C or further decrease in LDL-C and non-HDL-C than LOVAZA® are required.

Fasting triglyceride levels have been found to be correlated with the risk of cardiovascular diseases and conditions. For example, high fasting triglycerides levels have been associated with an increased risk of myocardial infarction. Gaziano et al. (*Circulation*, 1997; 96:2520-2525) discusses fasting triglyceride levels as a risk factor for coronary heart disease. Love-Osborne et al. (*Pediatr Diabetes*, 2006: 7:205-210) discloses the role of elevated fasting triglyceride levels in the development of type 2 diabetes mellitus.

All references cited herein are incorporated by reference in their entirety.

SUMMARY OF THE INVENTION

The present invention provides a pharmaceutical composition comprising eicosapentaenoic acid (EPA) and docosapentaenoic acid (DPA), wherein the amount of EPA and DPA is about 55% or more by weight of the total amount of fatty acids, and wherein the ratio of DHA:DPA is no more than 1:1. The present invention also provides a pharmaceutical composition comprising eicosapentaenoic acid (EPA), docosapentaenoic acid (DPA), and docosahexaenoic acid (DHA), wherein the amount of EPA and DPA is about 55% or more by weight of the total amount of fatty acids, and wherein the ratio of DHA:DPA is no more than 1:1.

The present invention provides a method of reducing lipid parameters, such as triglyceride levels, in a subject in need thereof, comprising administering to the subject a composition comprising docosapentaenoic acid (DPA) in an amount of at least about 20 mg/day, alternatively at least about 30 mg/day, alternatively at least about 40 mg/day, alternatively at least about 50 mg/day, alternatively at least about 60 mg/day alternatively, at least about 70 mg/day alternatively at least about 75 mg/day, alternatively at least about 80 mg/day, alternatively at least about 90 mg/day, alternatively at least about 100 mg/day, alternatively at least about 120 mg/day, alternatively at least about 150 mg/day, alternatively at least about 200 mg/day, alternatively at least about 300 mg/day, or alternatively at least about 400 mg/day.

The present invention also provides a method of reducing triglyceride levels in a subject in need thereof, comprising administering to the subject a composition comprising at least about 45% docosapentaenoic acid (DPA) relative to the total amount of fatty acids present in the composition. In some alternative embodiments, the composition comprises at least about 45% or at least about 50% or at least about 55% or at least about 60% or at least about 65% or at least about 70% or at least about 75% or at least about 80% or at least about 85% or at least about 90% or at least about 95% of DPA. The present invention also provides a method of reducing triglyceride levels in a subject in need thereof, comprising administering to the subject a composition comprising no more than about 20% docosahexaenoic acid (DHA) relative to the total amount of fatty acids present in the composition. In some alternative embodiments, the composition comprises no more than about 15% or no more than about 12% or no more than about 10% or no more than about 8% or no more than about 7%, no more than about 6%, no more than about 5%, no more than about 4%, no more than about 3%, no more than about 2%, or no more than about 1% DHA relative to the total amount of fatty acids present in the composition.

Furthermore, the present invention also provides a method of reducing triglyceride levels in a subject in need thereof, comprising administering to the subject a composition comprising docosapentaenoic acid (DPA) in a significant or higher relative amount as compared to docosahexaenoic acid (DHA) such that the DPA:DHA ratio in the composition is 1:2 or greater. In some alternative embodiments, the ratio of DPA:DHA in the composition is at least 1:1, or at least 2:1 or at least 3:1, or at least 4:1 or at least 5:1.

The present invention also provides a method of reducing other lipid parameters, such as total cholesterol, low density lipoprotein cholesterol, non-HDL cholesterol, and free fatty acids, in a subject in need thereof, comprising administering to the subject an orally administrable composition comprising docosapentaenoic acid (DPA) in an amount of at least about 20 mg/day, alternatively at least about 30 mg/day, alternatively at least about 40 mg/day, alternatively at least about 50 mg/day, alternatively at least about 60 mg/day alternatively, at least about 70 mg/day alternatively at least about 75 mg/day, alternatively at least about 80 mg/day, alternatively at least about 90 mg/day, alternatively at least about 100 mg/day, alternatively at least about 120 mg/day, alternatively at least about 150 mg/day, alternatively at least about 200 mg/day, alternatively at least about 300 mg/day, or alternatively at least about 400 mg/day.

The present invention also provides a method of reducing other lipid parameters, such as total cholesterol, non-HDL cholesterol, low density lipoprotein cholesterol, and free fatty acids in a subject in need thereof, comprising administering to the subject a composition comprising at least about 45% docosapentaenoic acid (DPA) relative to the total amount of fatty acids present in the composition. In some alternative embodiments, the composition comprises at least about 45% or at least about 50% or at least about 55% or at least about 60% or at least about 65% or at least about 70% or at least about 75% or at least about 80% or at least about 85% or at least about 90% or at least about 95% of DPA. The present invention also provides a method of reducing other lipid parameters in a subject in need thereof, comprising administering to the subject a composition comprising no more than about 20% docosahexaenoic acid (DHA) relative to the total amount of fatty acids present in the composition. In some alternative embodiments, the composition comprises no more than about 15% or no more than about 12% or no more than about 10% or no more than about 8% or no more than about 7%, no more than about 6%, no more than about 5%, no more than about 4%, no more than about 3%, no more than about 2%, or no more than about 1% DHA relative to the total amount of fatty acids present in the composition.

Furthermore, the present invention also provides a method of reducing other lipid parameters, such as total cholesterol, non-HDL cholesterol, low density lipoprotein cholesterol, and free fatty acids in a subject in need therefore, comprising administering to the subject a composition comprising docosapentaenoic acid (DPA) in a significant or higher relative amount as compared to docosahexaenoic acid (DHA) such that the DPA:DHA ratio in the composition is 1:2 or greater. In some alternative embodiments, the ratio of DPA:DHA in the composition is at least 1:1, or at least 2:1 or at least 3:1, or at least 4:1 or at least 5:1.

The present invention provides methods of reducing one or more lipid parameter levels from a baseline lipid parameter level, wherein the lipid parameter is selected from the group consisting of: triglycerides, total cholesterol, apolipoprotein B (apo B), apolipoprotein C-III (apoC-III), and non-HDL cholesterol, comprising administration of any of the compositions of the present invention. The present invention provides methods of increase a lipid parameter level from a baseline lipid parameter level, wherein the lipid parameter is selected from the group consisting of: non-HDL cholesterol and apolipoprotein A (apoA).

The methods may relate to lipid parameters measured in a fasted state, or in a fed state.

BRIEF DESCRIPTION OF THE DRAWINGS

FIG. 1 shows the fasting plasma lipid values after seven days of dosing, relating to the study described in Example 33.

DETAILED DESCRIPTION OF THE INVENTION

Figure 2:
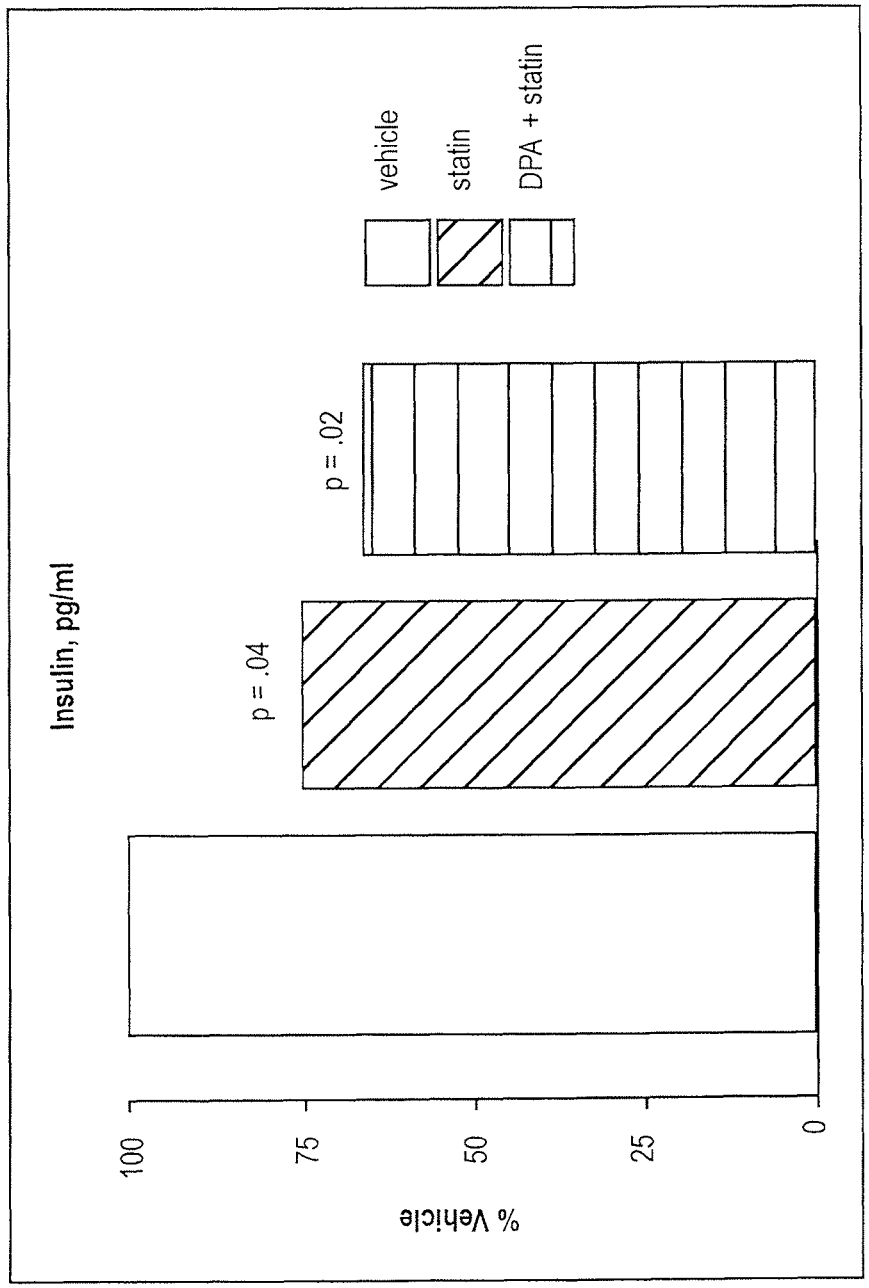
FIG. 2 shows the fasting plasma insulin levels after 28 days of administration, relating to the study described in Example 33.

The present invention provides a method of reducing lipid levels in a subject, preferably a human subject, comprising administration of docosapentaenoic acid (DPA). The lipids include, but are not limited to, triglycerides, total cholesterol, low density (LDL) lipoprotein, free fatty acids, and other lipoproteins that are not high-density lipoprotein (non-HDL). The present invention provides a method of increasing high-density lipoprotein (HDL) cholesterol in a subject, preferably a human subject, comprising administration of docosapentaenoic acid (DPA). The methods related to fasting or fed lipid levels. Fasting lipid levels refer to levels of the lipids in the plasma of a subject after a fasting period, which is a period of 8 to 12 hours without food.

In some embodiments, the baseline fasting triglyceride level in the subject prior to administration of DPA is greater than 150 mg/dL. In some embodiments, the baseline fasting triglyceride level is 150 mg/dL to 199 mg/dl, alternatively 200-499 mg/dL, alternatively over 500 mg/dL.

The DPA may be administered in an orally administrable composition comprising DPA. In some embodiments, the compositions comprise DPA in an amount between 1% and 99% relative to the total amount of fatty acids present in the composition, alternatively between 1% and 95%, alternatively between 1% and 90%, alternatively between 1% and 85%, alternatively between 1% and 80%, alternatively between 1% and 75%, alternatively between 1% and 70%, alternatively between 1% and 65%, alternatively between 1% and 60%, alternatively between 1% and 55%, alternatively between 1% and 50%, alternatively between 1% and 45%, alternatively between 1% and 40%, alternatively between 1% and 35%, alternatively between 1% and 30%, alternatively between 1% and 25%, alternatively between 1% and 20%, alternatively between 1% and 15%, alternatively between 1% and 10%, alternatively between 1% and 5%, alternatively between 2% and 99%, alternatively between 2% and 95%, alternatively between 2% and 90%, alternatively between 2% and 85%, alternatively between 2% and 80%, alternatively between 2% and 75%, alternatively between 2% and 70%, alternatively between 2% and 65%, alternatively between 2% and 60%, alternatively between 2% and 55%, alternatively between 2% and 50%, alternatively between 2% and 45%, alternatively between 2% and 40%, alternatively between 2% and 35%, alternatively between 2% and 30%, alternatively between 2% and 25%, alternatively between 2% and 20%, alternatively between 2% and 15%, alternatively between 2% and 10%, alternatively between 2% and 5%, alternatively between 3% and 99%, alternatively between 3% and 95%, alternatively between 3% and 90%, alternatively between 3% and 85%, alternatively between 3% and 80%, alternatively between 3% and 75%, alternatively between 3% and 70%, alternatively between 3% and 65%, alternatively between 3% and 60%, alternatively between 3% and 55%, alternatively between 3% and 50%, alternatively between 3% and 45%, alternatively between 3% and 40%, alternatively between 3% and 35%, alternatively between 3% and 30%, alternatively between 3% and 25%, alternatively between 3% and 20%, alternatively between 3% and 15%, alternatively between 3% and 10%, alternatively between 3% and 5%, alternatively between 4% and 99%, alternatively between 4% and 95%, alternatively between 4% and 90%, alternatively between 4% and 85%, alternatively between 4% and 80%, alternatively between 4% and 75%, alternatively between 4% and 70%, alternatively between 4% and 65%, alternatively between 4% and 60%, alternatively between 4% and 55%, alternatively between 4% and 50%, alternatively between 4% and 45%, alternatively between 4% and 40%, alternatively between 4% and 35%, alternatively between 4% and 30%, alternatively between 4% and 25%, alternatively between 4% and 20%, alternatively between 4% and 15%, alternatively between 4% and 10%, alternatively between 4% and 5%, alternatively between 5% and 99%, alternatively between 5% and 95%, alternatively between 5% and 90%, alternatively between 5% and 85%, alternatively between 5% and 80%, alternatively between 5% and 75%, alternatively between 5% and 70%, alternatively between 5% and 65%, alternatively between 5% and 60%, alternatively between 5% and 55%, alternatively between 5% and 50%, alternatively between 5% and 45%, alternatively between 5% and 40%, alternatively between 5% and 35%, alternatively between 5% and 30%, alternatively between 5% and 25%, alternatively between 5% and 20%, alternatively between 5% and 15%, alternatively between 5% and 12%, alternatively between 5% and 10%, alternatively between 6% and 99%, alternatively between 6% and 95%, alternatively between 6% and 90%, alternatively between 6% and 85%, alternatively between 6% and 80%, alternatively between 6% and 75%, alternatively between 6% and 70%, alternatively between 6% and 65%, alternatively between 6% and 60%, alternatively between 6% and 55%, alternatively between 6% and 50%, alternatively between 6% and 45%, alternatively between 6% and 40%, alternatively between 6% and 35%, alternatively between 6% and 30%, alternatively between 6% and 25%, alternatively between 6% and 20%, alternatively between 6% and 15%, alternatively between 6% and 12%, alternatively between 6% and 11%, alternatively between 6% and 10%, alternatively between 7% and 99%, alternatively between 7% and 95%, alternatively between 7% and 90%, alternatively between 7% and 85%, alternatively between 7% and 80%, alternatively between 7% and 75%, alternatively between 7% and 70%, alternatively between 7% and 65%, alternatively between 7% and 60%, alternatively between 7% and 55%, alternatively between 7% and 50%, alternatively between 7% and 45%, alternatively between 7% and 40%, alternatively between 7% and 35%, alternatively between 7% and 30%, alternatively between 7% and 25%, alternatively between 7% and 20%, alternatively between 7% and 15%, alternatively between 7% and 12%, alternatively between 7% and 11%, alternatively between 7% and 10%, alternatively between 8% and 99%, alternatively between 8% and 95%, alternatively between 8% and 90%, alternatively between 8% and 85%, alternatively between 8% and 80%, alternatively between 8% and 75%, alternatively between 8% and 70%, alternatively between 8% and 65%, alternatively between 8% and 60%, alternatively between 8% and 55%, alternatively between 8% and 50%, alternatively between 8% and 45%, alternatively between 8% and 40%, alternatively between 8% and 35%, alternatively between 8% and 30%, alternatively between 8% and 25%, alternatively between 8% and 20%, alternatively between 8% and 15%, alternatively between 8% and 12%, alternatively between 9% and 95%, alternatively between 9% and 90%, alternatively between 9% and 85%, alternatively between 9% and 80%, alternatively between 9% and 75%, alternatively between 9% and 70%, alternatively between 9% and 65%, alternatively between 9% and 60%, alternatively between 9% and 55%, alternatively between 9% and 50%, alternatively between 9% and 45%, alternatively between 9% and 40%, alternatively between 9% and 35%, alternatively between 9% and 30%, alternatively between 9% and 25%, alternatively between 9% and 20%, alternatively between 9% and 15%, alternatively between 9% and 12%, relative to the total amount of fatty acids present in the composition. In some embodiments, the compositions comprise DPA in an amount of at least about 45% of DPA. In some alternative embodiments, the composition comprises at least about 4% or at least about 8% or at least about 10% or at least about 20% or at least about 45% or at least about 50% or at least about 55% or at least about 60% or at least about 65% or at least about 70% or at least about 75% or at least about 80% or at least about 85% or at least about 90% or at least about 95% of DPA. In some embodiments, the composition comprises at least 20 mg of DPA, alternatively at least 30 mg, alternatively at least 40 mg, alternatively at least 50 mg, alternatively at least 60 mg, alternatively at least 90 mg, alternatively at least 100 mg, alternatively at least 120 mg, alternatively at least 150 mg, alternatively at least 200 mg, alternatively at least 300 mg, alternatively at least 400 mg of DPA. In some embodiments, the composition comprises DPA in a daily dosage of about 120 mg/day to about 150 mg/day, alternatively about 150 mg/day to about 200 mg/day, alternatively about 200 mg/day to about 250 mg/day, alternatively about 250 mg/day to about 300 mg/day, alternatively about 300 mg/day to about 400 mg/day, alternatively about 400 mg/day to about 600 mg/day, alternatively about 600 mg/day to about 1000 mg/day.

In some embodiments, the composition comprises DPA in ester form or in free fatty acid form.

In other embodiments, the compositions comprise docosapentaenoic acid (DPA) in a significant or higher relative amount as compared to docosahexaenoic acid (DHA) such that the DPA:DHA ratio in the composition is 1:2 or greater. In some alternative embodiments, the ratio of DPA:DHA in the composition is at least 1:1, or at least 2:1 or at least 3:1, or at least 4:1 or at least 5:1. The methods of treatment provides a dose of at least 20 mg DPA-N3, alternatively at least 30 mg DPA-N3, alternatively at least 40 mg DPA-N3, alternatively at least 50 mg DPA-N3, alternatively at least 60 mg DPA-N3 per day, alternatively at least 70 mg DPA-N3 per day, alternatively at least 75 mg DPA-N3 per day, alternatively at least 80 mg DPA-N3 per day, alternatively at least 90 mg DPA-N3 per day, alternatively at least 100 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 or its glycerol or ethyl esters per day. In some embodiments, the method of treatment provides a daily dose of at least about at least 20 mg of DPA, alternatively at least 30 mg, alternatively at least 40 mg, alternatively at least 50 mg, alternatively at least 60 mg, alternatively at least 90 mg, alternatively at least 100 mg, alternatively at least 120 mg, alternatively at least 150 mg, alternatively at least 200 mg, alternatively at least 300 mg, alternatively at least 350 mg, alternatively at least 400 mg of DPA. In some embodiments, the method of treatment provides a daily dose of at least about 1,000 mg DPA-N3 per day, alternatively at least about 1,500 mg DPA-N3 per day, alternatively at least about 2,000 mg DPA-N3 per day, alternatively at least about 2,500 mg DPA-N3 per day, alternatively at least about 3,000 mg DPA-N3 per day, alternatively at least about 3,500 mg DPA-N3 per day, alternatively at least about 3,750 mg DPA-N3 per day, alternatively at least about 4,000 mg DPA-N3 per day, alternatively at least about 4,250 mg DPA-N3 per day.

In some embodiments, the method of treatment provides a dose of at least about 1 mg/kg of DPA-N3 per day, alternatively about 2 mg/kg of DPA-N3 per day, alternatively about 3 mg/kg of DPA-N3 per day, alternatively about 4 mg/kg of DPA-N3 per day, alternatively about 6 mg/kg of DPA-N3 per day, alternatively about 8 mg/kg of DPA-N3 per day, alternatively about 10 mg/kg of DPA-N3 per day, alternatively about 20 mg/kg of DPA-N3 per day, alternatively about 30 mg/kg of DPA-N3 per day, and alternatively about 40 mg/kg alternatively about 50 mg/kg of DPA-N3 per day, alternatively about 75 mg/kg of DPA-N3 per day, and alternatively about 100 mg/kg.

The present invention provides an administrable composition comprising fatty acids, wherein at least 50% by weight of the fatty acids comprise omega-3-fatty acids, salts, esters, or derivatives thereof, wherein the omega-3 fatty acids comprise eicosapentaenoic acid (EPA; C20:5-n3), docosapentaenoic acid (DPA; C22:5-n3), and docosahexaenoic acid (DHA; C22:6-n3), wherein the ratio of DHA to EPA (DHA:EPA) is less than 1:20, and wherein the ratio of DHA to DPA (DHA:DPA) is less than 2:1.

In some embodiments, the compositions of the present invention comprise at least 50% omega-3 fatty acids, alternatively at least 55%, alternatively at least 60%, alternatively at least 65%, alternatively at least 70%, alternatively at least 75%, alternatively at least 80%, alternatively at least 85%, alternatively at least 95%, most preferably at least 90% omega-3 fatty acids of the total amount of fatty acids.

In other embodiments, EPA and DPA are jointly present in the compositions of the present invention at between about 55% and about 100% of total fatty acids, alternatively between about 60% and about 100%, alternatively between about 65% and about 100%, alternatively between about 70% and about 100%, alternatively between about 75% and about 100%, alternatively between about 80% and about 100%, alternatively between about 85% and about 95%, alternatively about 85% to about 100%, alternatively between about 85% and about 97%, alternatively between about 88% and about 95%, alternatively between about 88% and about 97%, alternatively about 88% to about 100%, alternatively between about 90% and about 95%, alternatively between about 90% and about 97%, alternatively about 90% to about 100%, alternatively about 95% to about 100%, alternatively about 97% to about 100% of the total amount of fatty acids.

The fatty acids, such as EPA and DPA, may be present in free fatty acid form, or as a salt, ester, or derivative. The fatty acids are preferably composed as a triglyceride, an ester (such as an ethyl ester) or free fatty acid. Other forms of the fatty acids which may be useful include salts, esters of any type, amides, mono-, di- or triglycerides, phospholipids or any other form which can lead to metabolization of the fatty acids (such as EPA and/or DPA), or the incorporation of the fatty acids (such as EPA and/or DPA) into body fluids, tissues or organs.

In some embodiments, the compositions of the present invention comprise at least 0.01% HPA of total fatty acids in the composition, alternatively at least 0.05% HPA, alternatively at least 0.10% HPA, alternatively at least 0.15% HPA, alternatively at least 0.2% HPA, alternatively at least 0.3% HPA, alternatively at least 0.4% HPA, alternatively at least 0.5% HPA, alternatively at least 0.75% HPA, alternatively at least 1% HPA, alternatively at least 1.5% HPA, alternatively at least 2% HPA, alternatively at least 2.5% HPA, alternatively at least 3% HPA, alternatively at least 3.5% HPA, alternatively at least 4% HPA, alternatively at least 4.5% HPA, alternatively at least 5% HPA, alternatively at least 6% HPA, alternatively at least 7% HPA, alternatively the compositions of the present invention comprise at least 9% HPA of total fatty acids in the composition.

In some embodiments, the compositions of the present invention comprise no more than 20% HPA of total fatty acids in the composition, alternatively no more than 15% HPA, alternatively no more than 12% HPA, alternatively no more than 10% HPA, alternatively no more than 8% HPA, alternatively no more than 7% HPA, alternatively no more than 6% HPA, alternatively no more than 5% HPA, alternatively no more than 4% HPA, alternatively no more than 3% HPA, alternatively no more than 2% HPA, alternatively no more than 1.5% HPA, alternatively the compositions of the present invention comprise at least 1% HPA of total fatty acids in the composition. In some embodiments, the compositions of the present invention comprise 1% to 20% of the total fatty acids in the composition.

In the embodiments of the present invention, the compositions comprise EPA and DPA in an EPA:DPA ratio between 99:1 and 1:99 EPA:DPA, alternatively between 90:1 and 1:90, alternatively between 60:1 and 1:60, alternatively between 60:1 and 1:20, alternatively between 60:1 and 1:4, alternatively between 40:1 and 1:20, alternatively between 30:1 and 1:20, alternatively between 30:1 and 1:10, alternatively between 30:1 and 1:5, alternatively between 40:1 and 1:4, alternatively between 30:1 and 1:4, alternatively between 30:1 and 1:2, alternatively between 30:1 and 1:1, alternatively between 30:1 and 2:1, alternatively between 30:1 and 5:1, alternatively between 20:1 and 1:20, alternatively between 20:1 and 1:10, alternatively between 20:1 and 1:5, alternatively between 20:1 and 1:2, alternatively between 20:1 and 1:1, alternatively between 20:1 and 2:1, alternatively between 20:1 and 5:1, alternatively between 20:1 and 10:1, alternatively between 20:1 and 10:1, alternatively between 30:1 and 10:1, alternatively between 60:1 and 10:1, alternatively comprise EPA and DPA in an EPA:DPA ratio between 40:1 and 10:1. In some embodiments, the ratio of EPA:DPA is greater than 1:1, preferably greater than 2:1, and more preferably greater than 5:1. In some embodiments, the ratio of EPA:DPA is 1:1 to 25:1, preferably 5:1 to 20:1, more preferably 8:1 to 15:1, even more preferably 9:1 to 13:1, even more most preferably about 10:1 to 11:1, and most preferably about 10:1.

In some embodiments, a relatively small amount of DHA relative to the total amount of fatty acids present in the composition is present. In some embodiments, the compositions of the present invention comprise no more than about 30% DHA, alternatively no more than about 20% DHA, alternatively no more than about 15% DHA, alternatively no more than about 12% DHA, alternatively no more than about 10% DHA, alternatively no more than about 8% DHA, alternatively no more than about 7% DHA, alternatively no more than about 6% DHA, alternatively no more than about 5% DHA, alternatively no more than about 4% DHA, alternatively no more than about 3% DHA, alternatively no more than about 2% DHA, alternatively no more than about 1% DHA relative to the total amount of fatty acids present in the composition.

In some embodiments, the ratio of DPA:HPA is about 250:1 to 1:1, alternatively 200:1 to 2:1, alternatively 150:1 to 3:1, alternatively 100:1 to 4:1, alternatively 50:1 to 5:1, alternatively 25:1 to 6:1, and alternatively 10:1 to 7:1. In some preferred embodiments, the ratio of DPA:HPA is about 8:1. In some embodiments, the ratio of DPA:HPA is about 3:0.

In other embodiments, a relatively small amount of DHA as compared to DPA is present. In these embodiments, the compositions of the present invention comprise no more than 15:1 of DHA:DPA, alternatively no more than 12:1 of DHA:DPA, alternatively no more than 10:1 of DHA:DPA, alternatively no more than 8:1 of DHA:DPA, alternatively no more than 5:1 of DHA:DPA, alternatively no more than 3:1 of DHA:DPA, alternatively no more than 2:1 of DHA:DPA, alternatively no more than 1:1 of DHA:DPA, alternatively no more than 1:2 of DHA:DPA, alternatively no more than 1:3 of DHA:DPA, alternatively no more than 1:4 of DHA:DPA, alternatively no more than 1:5 of DHA:DPA, alternatively no more than 1:6 of DHA:DPA, alternatively no more than 1:7 of DHA:DPA, alternatively no more than 1:8 of DHA:DPA, alternatively no more than 1:10 of DHA:DPA, alternatively no more than 1:12 of DHA:DPA, alternatively no more than 1:15 of DHA:DPA, alternatively no more than 1:20 of DHA:DPA, alternatively no more than 1:25 of DHA:DPA, alternatively no more than 1:50 of DHA:DPA, alternatively no more than 1:75 of DHA:DPA, alternatively no more than 1:90 of DHA:DPA, alternatively no more than 1:95 of DHA:DPA, alternatively no more than 1:100 of DHA:DPA. In some embodiments, the ratio of DHA:DPA is preferably less than 2:1.

In yet other embodiments, the compositions of the present invention comprise no more than 10% omega-6 fatty acids relative to the total amount of fatty acids, alternatively no more than 9%, alternatively no more than 8%, alternatively no more than 7%, alternatively no more than 6%, alternatively no more than 5%, alternatively no more than 4.5%, alternatively no more than 4%, alternatively no more than 3.5%, alternatively no more than 3%, alternatively no more than 2.5%, alternatively no more than 2%, alternatively no more than 1.7%, alternatively no more than 1.5%, alternatively no more than 1.2%, alternatively no more than 1%, alternatively no more than 0.5% omega-6 fatty acids versus the total amount of fatty acids comprised by the compositions of the present invention.

Omega-6 fatty acids include, but are not limited to: linoleic acid (LA; C18:2-n6); gamma-linoleic acid (GLA; C18:3-n6); eicosadienoic acid (C20:2-n6); dihomo-gamma-linoleic acid (DGLA; C20:3-n6); arachiconic acid (ARA; C20:4-n6); and omega-6 docosapentaenoic acid (DPA; C22:5-n6).

In further embodiments, the compositions of the present invention comprise no more than 10% omega-6 fatty acids relative to the total amount of omega-3 fatty acids plus omega-6 fatty acids, alternatively no more than 9%, alternatively no more than 8%, alternatively no more than 7%, alternatively no more than 6%, alternatively no more than 5%, alternatively no more than 4.5%, alternatively no more than 4%, alternatively no more than 3.5%, alternatively no more than 3%, alternatively no more than 2.5%, alternatively no more than 2%, alternatively no more than 1.7%, alternatively no more than 1.5%, alternatively no more than 1.2%, alternatively no more than 1%, alternatively no more than 0.5% omega-6 fatty acids versus the total amount of omega-3 fatty acids plus omega-6 fatty acids comprised by the compositions of the present invention.

In yet other embodiments, the compositions of the present invention comprise no more than 8% arachidonic acid (ARA; C20:4-n6) relative to the total amount of omega-3 fatty acids plus omega-6 fatty acids, alternatively no more than 7%, alternatively no more than 6%, alternatively no more than 5%, alternatively no more than 4.5%, alternatively no more than 4%, alternatively no more than 3.5%, alternatively no more than 3%, alternatively no more than 2.5%, alternatively no more than 2%, alternatively no more than 1.7%, alternatively no more than 1.5%, alternatively no more than 1.2%, alternatively no more than 1%, alternatively no more than 0.5% arachidonic acid (ARA; C20:4-n6) versus the total amount of omega-3 fatty acids plus omega-6 fatty acids comprised by the compositions of the present invention.

In some embodiments, a relatively small amount of omega-3 fatty acids in aggregate other than EPA, ETA, HPA and DPA (alternatively indicated as non-EPA, non-ETA, non-HPA and non-DPA omega-3 fatty acids in aggregate) relative to the total amount of fatty acids present in the composition is present. In some embodiments, the compositions of the present invention comprise no more than 20% non-EPA, non-ETA, non-HPA and non-DPA omega-3 fatty acids, alternatively no more than 15% non-EPA, non-ETA, non-HPA and non-DPA omega-3 fatty acids, alternatively no more than 12% non-EPA, non-ETA, non-HPA and non-DPA omega-3 fatty acids, alternatively no more than 10% non-EPA, non-ETA, non-HPA and non-DPA omega-3 fatty acids, alternatively no more than 8% non-EPA, non-ETA, non-HPA and non-DPA omega-3 fatty acids, alternatively no more than 7% non-EPA, non-ETA, non-HPA and non-DPA omega-3 fatty acids, alternatively no more than 6% non-EPA, non-ETA, non-HPA and non-DPA omega-3 fatty acids, alternatively no more than 5% non-EPA, non-ETA, non-HPA and non-DPA omega-3 fatty acids, alternatively no more than 4% non-EPA, non-ETA, non-HPA and non-DPA omega-3 fatty acids, alternatively no more than 3% non-EPA, non-ETA, non-HPA and non-DPA omega-3 fatty acids, alternatively no more than 2% non-EPA, non-ETA, non-HPA and non-DPA omega-3 fatty acids, alternatively no more than 1% non-EPA, non-ETA, non-HPA and non-DPA omega-3 fatty acids in aggregate relative to the total amount of fatty acids present in the composition.

In some embodiments, a relatively small amount of the sum of ALA, SDA and DHA relative to the total amount of fatty acids present in the composition is present, while at the same time large amounts of the sum of EPA, DPA-n3, HPA and ETA are present. In some embodiments, the compositions of the present invention comprise no more than 20% of the sum of ALA, SDA and DHA, alternatively no more than 15% of the sum of ALA, SDA and DHA, alternatively no more than 12% of the sum of ALA, SDA and DHA, alternatively no more than 10% of the sum of ALA, SDA and DHA, alternatively no more than 8% of the sum of ALA, SDA and DHA, alternatively no more than 7% of the sum of ALA, SDA and DHA, alternatively no more than 6% of the sum of ALA, SDA and DHA, alternatively no more than 5% of the sum of ALA, SDA and DHA, alternatively no more than 4% of the sum of ALA, SDA and DHA, alternatively no more than 3% of the sum of ALA, SDA and DHA, alternatively no more than 2% of the sum of ALA, SDA and DHA, alternatively no more than 1% of the sum of ALA, SDA and DHA relative to the total amount of fatty acids present in the composition, while at the same time contain more than 40% the sum of EPA, DPAn-3, HPA and ETA, alternatively more than 50% the sum of EPA, DPAn-3, HPA and ETA, alternatively more than 60% the sum of EPA, DPAn-3, HPA and ETA, alternatively more than 70% the sum of EPA, DPAn-3, HPA and ETA, alternatively more than 75% the sum of EPA, DPAn-3, HPA and ETA, alternatively more than 80% the sum of EPA, DPAn-3, HPA and ETA, alternatively more than 85% the sum of EPA, DPAn-3, HPA and ETA, alternatively more than 90% the sum of EPA, DPAn-3, HPA and ETA, alternatively more than 95% the sum of EPA, DPAn-3, HPA and ETA, alternatively between 80% and 98% the sum of EPA, DPAn-3, HPA and ETA, alternatively between 80% and 96% the sum of EPA, DPAn-3, HPA and ETA, alternatively between 85% and 98% the sum of EPA, DPAn-3, HPA and ETA, alternatively between 85% and 96% the sum of EPA, DPAn-3, HPA and ETA, alternatively between 90% and 98% the sum of EPA, DPAn-3, HPA and ETA, alternatively between 90% and 97% the sum of EPA, DPAn-3, HPA and ETA, alternatively between 90% and 96% the sum of EPA, DPAn-3, HPA and ETA, alternatively between 90% and 95% the sum of EPA, DPAn-3, HPA and ETA, relative to the total amount of fatty acids present in the composition is present.

In further embodiments, the compositions of the present invention comprise no more than 8% arachidonic acid (ARA; C20:4-n6) relative to the total amount of fatty acids, alternatively no more than 7%, alternatively no more than 6%, alternatively no more than 5%, alternatively no more than 4.5%, alternatively no more than 4%, alternatively no more than 3.5%, alternatively no more than 3%, alternatively no more than 2.5%, alternatively no more than 2%, alternatively no more than 1.7%, alternatively no more than 1.5%, alternatively no more than 1.2%, alternatively no more than 1%, alternatively no more than 0.5% arachidonic acid (ARA; C20:4-n6) relative the total amount of fatty acids comprised by the compositions of the present invention.

In other embodiments, the compositions of the present invention comprise no more than 2.5% arachidonic acid (ARA; C20:4-n6), no more than 0.4% omega-6-docosapentaenoic acid (DPA; C22:5-n6) and no more than 0.2% gamma-linoleic acid (GLA; C18:3-n6) relative the total amount of fatty acids comprised by the compositions of the present invention.

Further embodiments provide fatty acid compositions comprising no more than 2.5% arachidonic acid (ARA; C20:4-n6), no more than 0.3% omega-6 docosapentaenoic acid (DPA; C22:5-n6) and no more than 0.1% gamma-linoleic acid (GLA; C18:3-n6) relative the total amount of fatty acids comprised by the compositions of the present invention.

In yet other embodiments, the active ingredient of the formulations of the present invention consists essentially wholly of the EPA and DPA or precursors thereof (ethyl ester, triglyceride, or any other pharmaceutically acceptable salt or derivative thereof). In that case, no large amounts (preferably less than 15%, alternatively less than 12%, alternatively less than 10%, alternatively less than 9%, alternatively less than 8%, alternatively less than 7%, alternatively less than 6%, alternatively less than 5%, alternatively less than 4%, alternatively less than 3%, alternatively less than 2%, alternatively less than 1%, alternatively less than 0.5%, alternatively less than 0.25%) of any other fatty acids are present.

The fatty acid percentage is determined on a weight/weight, mol/mol, or chromatography area percent basis relative to all fatty acids present in the composition as determined by methods such as disclosed in the European Pharmacopeia monograph for omega-3 fatty acid concentrates, European Pharmacopeia monograph for omega-3-acid ethyl esters 90%, or European Pharmacopeia monograph method 2.4.29, USP monograph for fish oil dietary supplements, USP 35 omega-3-acid ethyl esters (LOVAZA®) monograph, or any essentially equivalent methods (whether by gas chromatography, HPLC, FPLC or any other chromatographic method).

In some embodiments, the fatty acid percentage is determined not as a percentage of all fatty acids present in the composition but as a specific type of fatty acid ethyl esters as percentage of all fatty acid ethyl esters present in the composition, thus excluding from the fatty acid percentage determination such fatty acids present as, for instance: free fatty acids; mono-, di-, and tri-glycerides; or fatty acids present in phospholipids (such as phosphatidylserine or phosphatidylcholine) or polysorbates (such as Tween 80, Tween 20, or polysorbate 40).

In other embodiments, the fatty acid percentage is determined not as a percentage of all fatty acids present in the composition but as a specific type of free fatty acid as percentage of all free fatty acids present in the composition, thus excluding from the fatty acid percentage determination such fatty acids present as, for instance: fatty acid ethyl esters; mono-, di-, and tri-glycerides; or fatty acids present in phospholipids (such as phosphatidylserine or phosphatidylcholine) or polysorbates (such as Tween 80, Tween 20, or polysorbate 40).

In yet other embodiments, the fatty acid percentage is determined not as a percentage of all fatty acids present in the composition but as a specific type of glycerol fatty acid ester as percentage of all glycerol fatty acid esters present in the composition, thus excluding from the fatty acid percentage determination such fatty acids present as, for instance: fatty acid ethyl esters; free fatty acids; or fatty acids present in phospholipids (such as phosphatidylserine or phosphatidylcholine) or polysorbates (such as Tween 80, Tween 20, or polysorbate 40).

In further embodiments, the fatty acid percentage is determined not as a percentage of all fatty acids present in the composition but as di- or tri-fatty acid esters with glycerol as percentage of all glycerol di- and tri-fatty acid esters present in the composition, thus excluding from the fatty acid percentage determination such fatty acids present as, for instance: glycerol-mono-fatty acid esters; fatty acid ethyl esters; free fatty acids; or fatty acids present in phospholipids (such as phosphatidylserine or phosphatidylcholine) or polysorbates (such as Tween 80, Tween 20, or polysorbate 40).

In yet other embodiments, the fatty acid percentage is determined not as a percentage of all fatty acids present in the composition but as a tri-fatty acid esters with glycerol as percentage of all glycerol tri-fatty acid esters present in the composition, thus excluding from the fatty acid percentage determination such fatty acids present as, for instance: mono- and di-fatty acid esters of glycerol; fatty acid ethyl esters; free fatty acids; or fatty acids present in phospholipids (such as phosphatidylserine or phosphatidylcholine) or polysorbates (such as Tween 80, Tween 20, or polysorbate 40).

The EPA, HPA, DPA, or omega-3-pentaenoic acids may be derived from any appropriate source including plant seed oils, microbial oils from algae or fungal or marine oils from fish or other marine animals. Certain species are a particular good source of oils containing DPA, for example seal oil. They may be used in the form of the natural oil, if that oil meets the required purity requirements of the present invention, or may be purified to give products containing the fatty acid composition of the present invention.

The compositions of the present invention may be produced through a range of the methods. Such methods may include: distillation, including short path distillation; urea precipitation; enzymatic conversion concentration; conventional chromatography; HPLC/FPLC; supercritical carbondioxide extraction; supercritical carbondioxide chromatography; simulated moving bed chromatography; supercritical carbondioxide simulated moving bed chromatography; or chemical conversion methods such as iodolactonization. Such methods are generally known to those skilled in the art of purifying and isolating omega-3 fatty acids.

Typically, the omega-3 fatty acid concentration/purification process is initiated by esterifying the fatty acids comprised by the marine oil raw material (such as crude fish oil) with ethanol (to form fatty acid ethyl esters) in order to separate omega-3 fatty acids from other fatty acids covalently bound together in the natural triglyceride molecules of the source oil. Subsequently, the material may be distilled once or several times to achieve omega-3-acid ethyl ester concentrations above 60%-70%. Alternatively, enzymatic concentration, urea precipitation or supercritical extraction may be used alone or in conjunction with distillation to reach omega-3 levels above 70%-90%. In order to prepare a highly pure concentrate of a single omega-3 fatty acid, methods such as chromatography, supercritical chromatography, simulated moving bed chromatography, supercritical simulated moving bed chromatography, or chemical conversion methods such as iodolactolization are typically most practical to reach levels above 50%, alternatively above 60%, alternatively above 70%, alternatively above 80%, alternatively above 90%, alternatively above 95%, of a single omega-3 fatty acid such as ETA, EPA, HPA, DPA, TPA, or DHA.

Those skilled in the art will be able to design processes suited to prepare a certain omega-3 fatty acid composition as desired, based on the methods described above. Such processes are flexible enough to affect the relative proportions between the long chain C18, C20, C21 and C22 fatty acids which occur naturally in available fish oil raw materials and other marine oils. It provides not only for the concentration of the individual omega-3 fatty acids, but the ratio between them will remain within a pattern of variation caused by variations in nature. However, suitable methods compensate for sometimes extreme variations which may occur naturally. Thus, for those skilled in the art, it will be possible to make a product with a constant and predetermined composition.

EPA is relatively abundant in fish oils or other marine oils and can be relatively easy obtained through the application of concentration and purification technologies from such fish or marine oils. DPA and HPA are present at much lower concentrations. In order to prepare the compositions of the present invention, DPA or HPA may be concentrated and purified from fish or other marine oils according to the methods referred to above, either alone or DPA combined with EPA and/or HPA. Alternatively, the DPA or HPA may be chemically prepared from a high purity EPA concentrate by elongation of the EPA fatty-acid chain with two or one hydrogen-saturated carbons (C2-elongation or C1-elongation) on the carboxyl side of the molecule (for instance with a method similar to or alternate methods with equivalent results such as described by Kuklev D V and Smith W L in Chem Phys Lipids, 2006; 144(2): 172-177). In another alternative approach, a high purity EPA concentrate may be partially converted to DPA (or HPA) using a method for C2-elongation (or C1-elongation) of EPA similar to those described above, thus directly yielding compositions of the present invention or intermediates therefore.

Once the oils containing one or more of the desired fatty acids have been obtained, and purified as necessary, these oils may be blended to give the desirable relative amounts of EPA, DPA, HPA, DHA, TPA, other omega-3 fatty acids and omega-6 fatty acids to obtain the compositions of the present invention described in detail above.

Fish oils may also contain by-products and contaminants such as pesticides, chlorinated or brominated hydrocarbons, heavy metals, cholesterol and vitamins. During the production of the concentrate, the concentrations of these components are significantly reduced compared to untreated fish oils. Such reduction is inherent due to the nature of purification methods and their ability to concentrate of several or specific omega-3 fatty acids, thus removing other compounds.

Triglycerides comprising more than 60% of the omega-3 fatty acids in the composition may be produced from ethyl esters and glycerol by well known, published, or alternative chemical synthetic or enzymatic procedures. The free acids may be produced from ethyl esters by well known hydrolization or saponification procedures. Methods for converting ethyl esters to triglycerides, free fatty acids, and other molecular forms comprising fatty acids, are generally known to those skilled in the art chemically or enzymatically converting omega-3 fatty acids from one form to another.

The compositions of the present invention may be used for the treatment of patients by administering an effective amount of such compositions to a subject in need thereof, such as a subject prone to or afflicted with a disease or condition or in need of treatment for a disease or condition. The present invention provides methods of treating, preventing, and reducing symptoms associated with a disease or condition comprising administration of a composition of the present invention. Exemplary diseases or conditions include, but are not limited to: hypertriglyceridemia (for example, by those skilled in the art typically established by assessing fasting triglyceride (TG) levels); hypertriglyceridemia with TG≥500 mg/dL (VHTG); hypertriglyceridemia with TG 200-499 mg/dL; hypertriglyceridemia with TG 200-499 mg/dL while on statin treatment (HTG); hypercholesterolemia; mixed dyslipidemia; coronary heart disease (CHD); vascular disease; atherosclerotic disease and related conditions; heart failure; cardiac arrhythmias; blood coagulatory conditions associated with cardiac arrhythmias; hypertension; coagulation related disorders, including post-surgical deep vein thrombosis or other high risk thrombosis conditions; nephropathy; kidney or urinary tract disease; retinopathy; cognitive, psychiatric, neurological and other CNS disorders, including but not limited to schizophrenia, depression, bipolar disorder and any form of dementia (including ischemic dementia and vascular dementia); autoimmune diseases; inflammatory diseases; asthma, COPD or other respiratory disease; dermatological disease; metabolic syndrome; diabetes or other forms of metabolic disease; liver diseases including fatty liver disease; diseases affecting the senses, including those affecting vision and hearing; diseases of the gastrointestinal tract; diseases of the male or female reproductive system or related secondary sexual organs; a cancer of any type, including lymphomas, myelomas and solid tumor cancers;

any infections caused by a virus, bacterium, fungus, protozoa or other organism. The present invention also provides for the treatment and/or prevention of cardiac events and/or cardiovascular events and/or vascular events and/or symptoms. The present invention also provides for the reduction of number of such events, as well as a reduction or amelioration of symptoms associated with such events.

Cardiovascular and/or cardiac events may include, but are not limited to: myocardial infarction, ischemic cardiac attack, ischemic attack, acute angina, hospitalization due to acute angina, stroke, transient ischemic cerebral attack, cardiac revascularization, cardiac revascularization with stent placement, carotid artery revascularization, carotid artery revascularization with stent placement, peripheral artery revascularization, peripheral artery revascularization with stent placement, plaque rupture, death due to cardiovascular event, and hospitalization due to cardiovascular event. Cardiovascular and/or cardiac events may also include other events deemed to fall in such catergory by those skilled in the art.

The present invention provides methods of treatment for hypertriglyceridemia (either TG≥500 mg/dL, TG≥200 mg/dL, TG≥150 mg/dL, TG200-499 mg/dL, TG300-499 mg/dL, TG350-499 mg/dL, or TG150-199 mg/dL), mixed dyslipidemia, or any other diseases or medical conditions as specified above, by dosing to a subject in need thereof omega-3 docosapentaenoic acid (DPA-n3) or its glycerol or ethyl esters. The present invention also provides for a method for reducing fasting lipid parameters, such as triglycerides, low-density lipoprotein (LDL) cholesterol, total cholesterol, non-HDL cholesterol, free fatty acids, and total non-high-lipoprotein cholesterol (non-HDL) cholesterol. The present invention also provides method for increasing high-lipoprotein (HDL) cholesterol levels. The methods of treatment provides a dose of at least 60 mg DPA-N3 per day, alternatively at least 80 mg DPA-N3 per day, alternatively at least 90 mg DPA-N3 per day, alternatively at least 100 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 or its glycerol or ethyl esters per day. In some embodiments, the method of treatment provides a dose of at least about 1,000 mg DPA-N3 per day, alternatively at least about 1,500 mg DPA-N3 per day, alternatively at least about 2,000 mg DPA-N3 per day, alternatively at least about 2,500 mg DPA-N3 per day, alternatively at least about 3,000 mg DPA-N3 per day, alternatively at least about 3,500 mg DPA-N3 per day, alternatively at least about 3,750 mg DPA-N3 per day, alternatively at least about 4,000 mg DPA-N3 per day, alternatively at least about 4,250 mg DPA-N3 per day.

In other embodiments, the compositions comprise docosapentaenoic acid (DPA) in a significant or higher relative amount as compared to docosahexaenoic acid (DHA) such that the DPA:DHA ratio in the composition is 1:2 or greater. In some alternative embodiments, the ratio of DPA:DHA in the composition is at least 1:1, or at least 2:1 or at least 3:1, or at least 4:1 or at least 5:1.

In some embodiments, the method of treatment provides a dose of at least about 1 mg/kg of DPA-N3 per day, alternatively about 2 mg/kg of DPA-N3 per day, alternatively about 3 mg/kg of DPA-N3 per day, alternatively about 4 mg/kg of DPA-N3 per day, alternatively about 6 mg/kg of DPA-N3 per day, alternatively about 8 mg/kg of DPA-N3 per day, alternatively about 10 mg/kg of DPA-N3 per day, alternatively about 20 mg/kg of DPA-N3 per day, alternatively about 30 mg/kg of DPA-N3 per day, and alternatively about 40 mg/kg alternatively about 50 mg/kg of DPA-N3 per day, alternatively about 75 mg/kg of DPA-N3 per day, and alternatively about 100 mg/kg.

In some embodiments, the compositions of the present invention, which may comprise significant amounts of omega-3 docosapentaenoic acid (DPA-n3) or its glycerol or ethyl esters, may be used for the treatment of hypertriglyceridemia (either TG≥500 mg/dL, TG≥200 mg/dL, TG≥150 mg/dL, TG200-499 mg/dL, TG300-499 mg/dL, TG350-499 mg/dL, or TG150-199 mg/dL), mixed dyslipidemia, or any other diseases or medical conditions specified above. Such method of treatment provides to a subject in need thereof a dose of at least 20 mg DPA-N3 per day, alternatively at least 25 mg DPA-N3 per day, alternatively at least 30 mg DPA-N3 per day, alternatively at least 40 mg DPA-N3 per day, alternatively at least 50 mg DPA-N3 per day, alternatively at least 60 mg DPA-N3 per day, alternatively at least 70 mg DPA-N3 per day, alternatively at least 80 mg DPA-N3 per day, alternatively at least 90 mg DPA-N3 per day, alternatively at least 100 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 or its glycerol or ethyl esters per day. In some embodiments, the methods of the present invention relate to decreasing plasma lipid parameters in a subject in need thereof. The lipid parameters may be measured in a fasting state or a fed state. In some embodiments, the methods comprise administration of DPA in the free fatty acid form or an ester form. In some embodiments, the methods comprise a reduction in triglyceride levels of at least 10%, alternatively at least 15%, alternatively at least 20%, alternatively at least 25%, alternatively at least 30%, alternatively at least 35%, alternatively at least 40%, alternatively at least 45%, and alternatively at least 50% compared to baseline. In some embodiments, the methods comprise a reduction in total cholesterol levels of at least 1%, alternatively at least 2%, alternatively at least 3%, alternatively at least 4%, alternatively at least 5%, alternatively at least 6%, alternatively at least 7%, alternatively at least 8%, alternatively at least 9%, alternatively at least 10% compared to baseline. In some embodiments, the methods comprise a reduction in low-density lipoprotein (LDL) levels of at least 10%, alternatively at least 15%, alternatively at least 20%, alternatively at least 25%, alternatively at least 30%, alternatively at least 35%, alternatively at least 40%, alternatively at least 45%, and alternatively at least 50% compared to baseline. In some embodiments, the methods comprise a reduction in free fatty acid levels of at least 5%, alternatively at least 7%, alternatively at least 10%, alternatively at least 15%, alternatively at least 20% compared to baseline. In some embodiments, the methods comprise a reduction in non-HDL cholesterol levels of at least 1%, alternatively at least 2%, alternatively at least 3%, alternatively at least 4%, alternatively at least 5%, alternatively at least 6%, alternatively at least 7%, alternatively at least 8%, alternatively at least 9%, alternatively at least 10% compared to baseline. In some embodiments, the methods comprise an increase in high density lipoprotein (HDL) cholesterol levels of at least 1%, alternatively at least 2%, alternatively at least 3%, alternatively at least 4%, alternatively at least 5%, alternatively at least 6%, alternatively at least 7%, alternatively at least 8%, alternatively at least 9%, alternatively at least 10% compared to baseline. In some embodiments, this change in lipid parameters can be achieved after a period of daily administration, such as one week, alternatively one month, alternatively two months, alternatively three months or more.

In other embodiments, the compositions of the present invention, which may comprise significant amounts of omega-3 docosapentaenoic acid (DPA-n3) or its glycerol or ethyl esters and which comprise relatively small amounts of omega-3 docosahexaenoic acid (DHA-n3), may be used for the treatment of hypertriglyceridemia (either TG≥500 mg/dL, TG≥200 mg/dL, TG≥150 mg/dL, TG200-499 mg/dL, TG300-499 mg/dL, TG350-499 mg/dL, or TG150-199 mg/dL), mixed dyslipidemia, or any other diseases or medical conditions specified above. Such method of treatment provides to a subject in need thereof a dose of at least 20 mg DPA-N3 per day, alternatively at least 25 mg DPA-N3 per day, alternatively at least 30 mg DPA-N3 per day, alternatively at least 40 mg DPA-N3 per day, alternatively at least 50 mg DPA-N3 per day, alternatively at least 60 mg DPA-N3 per day, alternatively at least 80 mg DPA-N3 per day, alternatively at least 90 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 or its glycerol or ethyl esters per day, while providing less than 1500 mg of DHA, alternatively less than 1200 mg of DHA, alternatively less than 1000 mg of DHA, alternatively less than 800 mg of DHA, alternatively less than 700 mg of DHA, alternatively less than 600 mg of DHA, alternatively less than 500 mg of DHA, alternatively less than 400 mg of DHA, alternatively less than 350 mg of DHA, alternatively less than 300 mg of DHA, alternatively less than 250 mg of DHA, alternatively less than 200 mg of DHA alternatively less than 150 mg of DHA, alternatively less than 120 mg of DHA, alternatively less than 100 mg of DHA, alternatively less than 80 mg of DHA, alternatively less than 60 mg of DHA, alternatively less than 40 mg of DHA, alternatively less than 30 mg of DHA, alternatively less than 25 mg of DHA, alternatively less than 20 mg of DHA or its glycerol or ethyl esters per day. In further embodiments, the compositions of the present invention, which may comprise significant amounts of omega-3 docosapentaenoic acid (DPA-n3) or its glycerol or ethyl esters and which comprise relatively small amounts of omega-3 docosahexaenoic acid (DHA-n3), may be used for the treatment of hypertriglyceridemia (either TG≥500 mg/dL, TG≥200 mg/dL, TG≥150 mg/dL, TG200-499 mg/dL, TG300-499 mg/dL, TG350-499 mg/dL, or TG150-199 mg/dL), mixed dyslipidemia, or any other diseases or medical conditions specified above. Such method of treatment provides to a subject in need thereof a dose of at least 30 mg DPA-N3 per day, alternatively at least 40 mg DPA-N3 per day, alternatively at least 50 mg DPA-N3 per day, alternatively at least 60 mg DPA-N3 per day, alternatively at least 80 mg DPA-N3 per day, alternatively at least 90 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 per day, alternatively at least 1000 mg DPA-N3 per day, alternatively at least 1200 mg DPA-N3 per day, alternatively at least 1500 mg DPA-N3 or its glycerol or ethyl esters per day, while providing a relatively small amount of DHA-N3 such that the DHA:DPA dose ratio is no more than 15:1 of DHA:DPA, alternatively no more than 12:1 of DHA:DPA, alternatively no more than 10:1 of DHA:DPA, alternatively no more than 8:1 of DHA:DPA, alternatively no more than 5:1 of DHA:DPA, alternatively no more than 3:1 of DHA:DPA, alternatively no more than 2:1 of DHA:DPA, alternatively no more than 1:1 of DHA:DPA, alternatively no more than 1:2 of DHA:DPA, alternatively no more than 1:3 of DHA:DPA, alternatively no more than 1:5 of DHA:DPA, alternatively no more than 1:8 of DHA:DPA, alternatively no more than 1:10 of DHA:DPA, alternatively no more than 1:15 of DHA:DPA, alternatively a relative daily dose of no more than 1:20 of DHA:DPA.

In some embodiments, the improved profile of the compositions of the present invention may be demonstrated upon treatment of a subject by differentially altering the ration between blood platelets and fragments thereof (also known as platelet microparticles). Such fragments may be evaluated as a whole or examined and described as fragment sub-categories.

In other embodiments, the improved profile of the compositions of the present invention may be demonstrated upon treatment of a subject by differentially altering the surface charge of blood platelets and fragments thereof, either in resting state (non-activated platelets) or activated stage.

In yet other embodiments, treatment of a subject or patient with compositions of the present invention affect the coagulatory cascade and differentially alter coagulation or bleeding times or platelet aggregation times and density.

In further embodiments, treatment with compositions of the present invention improves the vascular healing process in response to atherogenic disease. Such healing may be demonstrated by reduced stenosis and/or restenosis over time, reduced or lesser increase in intima-media thickness (IMT) of the arterial wall, larger lumen size and/or larger vascular diameter at vascular sites with stenosis or clot built-up, as determined by either by intravascular ultrasound (IVUS), radiographic, radiologic, non-invasive ultrasound, tomography, magnetic resonance interference (MRI), or other acceptable methods. In other embodiments, such improved healing may be demonstrated by the vascular wall composition, such as a reduced foam cell presence or fibrillated tissue in the vessel wall. In yet other embodiments, such improved vascular healing is demonstrated by improved inflammatory markers in the vascular wall.

The improved profile resulting from treatment with the compositions of the present invention may also be demonstrated by a differentiated impact on blood/serum/plasma lipid and lipoprotein levels in a mammal; these include, but are not limited to: Triglycerides (TG), total-cholesterol, non-HDL-cholesterol, LDL-cholesterol, VLDL-cholesterol, apolipoprotein B, apolipoprotein A, apolipoprotein C-III, HDL-cholesterol, and Lp-PLA2. The compositions of the present invention may also be used to provide a beneficial impact on the one or more of the following: apolipoprotein A-I (apo A-I), apolipoprotein B (apo B), apo A-I/apo B ratio, lipoprotein(a) (Lp[a]), lipoprotein-associated phospholipase A2 (Lp-PLA2), low density lipoprotein (LDL) particle number and size, oxidized LDL, C-reactive protein (CRP), high sensitivity C-reactive protein (HSCRP), intracellular adhesion molecule-1 (ICAM-1), E-selectin, P-selectin, vascular cell adhesion molecule 1 (VCAM-1) or cluster of differentiation 106 (CD106), interleleukin-1β (IL-1β), interleukin-2 (IL-2), interleukin-6 (IL-6), interleukin-8 (IL-8), interleukin-10 (IL-10), interleukin-12 (IL-12), interleukin-15 (IL-15), interleukin-18 (IL-18), tumor necrosis factor-alpha (TNF-α), tumor necrosis factor-beta (TNF-β), plasminogen activator inhibitor-1 (PAI-1), homocysteine, thromboxane B2 (TXB2), thromboxane A2 (TXA2), 2,3-dinor thromboxane B2, free fatty acids (FFA), serum amyloid A1, serum amyloid A2, serum amyloid A3, serum amyloid A4, thiobarbituric acid (TBA) reacting material, adiponectin (GBP-28), hemoglobin A1c (HbA1c), macrophage colony stimulating factor (M-CSF), granulocyte macrophage colony stimulating factor (GM-CSF), fibrinogen, fibrin D-dimer, platelet derived-microparticles, mean platelet volume (MPV), platelet subpopulations, heart rate, systolic and diastolic blood pressure, nuclear factor kappa-light-chain enhancer of activated B cells (NF-κβ), adenosine diphosphate induced platelet aggregation, platelet endothelial cell adhesion molecule (PECAM-1), vitronectin receptor ($\alpha_v\beta_v$), and glycoprotein IIb/IIIa (gpIIIb/IIIa). The compositions of the present invention may also be used in methods of treating, preventing, and reducing symptoms associated with conditions associated with the above.

Methods to determine comparative blood/serum/plasma lipid and lipoprotein levels and therapeutic effects on these levels in mammals are generally know to those skilled in the art and are typically based on fasting lipid and lipoprotein levels. Differences of active treatment versus placebo are generally assessed on a group of subjects versus another group of subjects basis, with significant changes noted if the p-value for the appropriate statistical comparison is equal to or less than 0.05. P-values larger than 0.05 but equal to or less than 0.10 may be considered borderline significant (BS). P-values larger than 0.10 are generally considered not significant (NS). In one embodiment, treatment with the compositions of the present invention is more potent than other omega-3 compositions known in the prior art (such as LOVAZA®, EPANOVA™ or AMR101) in reducing as compared to placebo or baseline: TG levels, Total-cholesterol levels, non-HDL-cholesterol levels, VLDL-cholesterol levels, LDL-cholesterol levels, apolipoprotein B levels, apolipoprotein C-III levels, Lp-PLA2 levels, or any combinations thereof. In other embodiments, such more potent effects in reducing these pararemeters are achieved in patients with baseline TG over 500 mg/dL, in patients on statin treatment with baseline TG in the 200-499 mg/dL range, in patients not on statin treatment with baseline LDL-cholesterol of 190 mg/dL or higher and with TG in the 300-700 mg/dL range, in patients not on statin treatment with baseline LDL-cholesterol of 190 mg/dL or higher and with TG in the 350-700 mg/dL range, in patients not on statin treatment with baseline LDL-cholesterol of 190 mg/dL or higher and with TG in the 300-750 mg/dL range, in patients not on statin treatment with baseline LDL-cholesterol of 190 mg/dL or higher and with TG in the 350-750 mg/dL range, or in patients not on statin treatment with baseline non-HDL-cholesterol of 200 mg/dL or higher and with TG in the 300-700 mg/dL range, or in patients not on statin treatment with baseline non-HDL-cholesterol of 200 mg/dL or higher and with TG in the 350-700 mg/dL range, or in patients not on statin treatment with baseline non-HDL-cholesterol of 200 mg/dL or higher and with TG in the 300-750 mg/dL range, or in patients not on statin treatment with baseline non-HDL-cholesterol of 200 mg/dL or higher and with TG in the 350-750 mg/dL range.

In a further embodiment, treatment with the compositions of the present invention together with statin therapy is more potent than other omega-3 compositions known in the prior art (such as LOVAZA®, EPANOVA™ or AMR101) in reducing as compared to placebo or baseline: TG levels, Total-cholesterol levels, non-HDL-cholesterol levels, VLDL-cholesterol levels, LDL-cholesterol levels apolipoprotein B levels, apolipoprotein C-III levels, Lp-PLA2 levels, or any combinations thereof. In other embodiments, such more potent effects in reducing these pararemeters are achieved in patients with baseline TG over 500 mg/dL, in patients on statin treatment with baseline TG in the 200-499 mg/dL range, in patients not on baseline statin treatment with baseline LDL-cholesterol of 190 mg/dL or higher and with TG in the 300-700 mg/dL range, in patients not on baseline statin treatment with baseline LDL-cholesterol of 190 mg/dL or higher and with TG in the 350-700 mg/dL range, in patients not on baseline statin treatment with baseline LDL-cholesterol of 190 mg/dL or higher and with TG in the 300-750 mg/dL range, in patients not on baseline statin treatment with baseline LDL-cholesterol of 190 mg/dL or higher and with TG in the 350-750 mg/dL range, or in patients not on baseline statin treatment with baseline non-HDL-cholesterol of 200 mg/dL or higher and with TG in the 300-700 mg/dL range, or in patients not on baseline statin treatment with baseline non-HDL-cholesterol of 200 mg/dL or higher and with TG in the 350-700 mg/dL range, or in patients not on baseline statin treatment with baseline non-HDL-cholesterol of 200 mg/dL or higher and with TG in the 300-750 mg/dL range, or in patients not on baseline statin treatment with baseline Non-HDL-cholesterol of 200 mg/dL or higher and with TG in the 350-750 mg/dL range.

The present invention also provides methods of reducing triglycerides levels in a subject, wherein the non-HDL cholesterol levels, such as LDL-cholesterol levels, of the subject are reduced or not significantly increased from, for example, baseline levels before treatment. In some embodiments, treatment with the compositions of the present invention results in a minor (less than 10% change from baseline, alternatively less than 5%) and/or non-significant change in non-HDL cholesterol levels (such as LDL-cholesterol levels) as compared to placebo in patients with baseline TG levels above 500 mg/dL. In a further embodiment, treatment with the compositions of the present invention results in reductions of LDL-cholesterol levels as compared to placebo in patients with baseline TG levels above 500 mg/dL. In some embodiments, the methods involve coadministration of a statin.

In another embodiment, treatment with the compositions of the present invention as compared to placebo does not increase LDL-cholesterol levels in patients with baseline TG levels of 200-499 mg/dL while on statin therapy.

In yet another embodiment, treatment with the compositions of the present invention as compared to placebo results in significant reductions in LDL-cholesterol levels in patients with baseline TG levels of 200-499 mg/dL while on statin therapy.

In a further embodiment, the compositions of the present invention as compared to placebo result in significant reductions in LDL-cholesterol levels in patients not on statin treatment with LDL-cholesterol of 190 mg/dL or higher and with TG in the 300-700 mg/dL range, in patients not on statin treatment with LDL-cholesterol of 190 mg/dL or higher and with TG in the 350-700 mg/dL range, in patients not on statin treatment with LDL-cholesterol of 190 mg/dL or higher and with TG in the 300-750 mg/dL range, or in patients not on statin treatment with LDL-cholesterol of 190 mg/dL or higher and with TG in the 350-750 mg/dL range. Finally, another embodiment, the compositions of the present invention as compared to placebo result in significant reductions in LDL-cholesterol levels in patients not on statin treatment with non-HDL-cholesterol of 200 mg/dL or higher and with TG in the 300-700 mg/dL range, in patients not on statin treatment with Non-HDL-cholesterol of 200 mg/dL or higher and with TG in the 350-700 mg/dL range, in patients not on statin treatment with non-HDL-cholesterol of 200 mg/dL or higher and with TG in the 300-750 mg/dL range, or in patients not on statin treatment with Non-HDL-cholesterol of 200 mg/dL or higher and with TG in the 350-750 mg/dL range.

In another embodiment, treatment with the compositions of the present invention together with statin therapy results in significant reductions in LDL-cholesterol levels as compared to placebo in patients not on statin treatment at baseline with baseline LDL-cholesterol of 190 mg/dL or higher and with TG in the 300-700 mg/dL range, in patients not on baseline statin treatment with baseline LDL-cholesterol of 190 mg/dL or higher and with TG in the 350-700 mg/dL range, in patients not on baseline statin treatment with baseline LDL-cholesterol of 190 mg/dL or higher and with TG in the 300-750 mg/dL range, or in patients not on baseline statin treatment with baseline LDL-cholesterol of 190 mg/dL or higher and with TG in the 350-750 mg/dL range.

Finally, another embodiment, treatment with the compositions of the present invention together with statin therapy results in significant reductions in LDL-cholesterol levels as compared to placebo in patients not on baseline statin treatment with baseline non-HDL-cholesterol of 200 mg/dL or higher and with TG in the 300-700 mg/dL range, in patients not on baseline statin treatment with baseline non-HDL-cholesterol of 200 mg/dL or higher and with TG in the 350-700 mg/dL range, in patients not on baseline statin treatment with baseline non-HDL-cholesterol of 200 mg/dL or higher and with TG in the 300-750 mg/dL range, or in patients not on baseline statin treatment with baseline Non-HDL-cholesterol of 200 mg/dL or higher and with TG in the 350-750 mg/dL range.

In another embodiment, the compositions of the present invention are more potent than other omega-3 compositions known in the prior art (such as LOVAZA®, EPANOVA™ or AMR101) in increasing as compared to placebo or baseline HDL-cholesterol levels, apolipoprotein-A levels, or a combination thereof.

In yet another embodiment, the compositions of the present invention are more potent than other omega-3 compositions known in the prior art (such as LOVAZA®, EPANOVA™ or AMR101) in decreasing as compared to placebo or baseline Apolipoprotein-B (Apo-B) levels, Apolipoprotein-CIII levels, Lp-PLA2 levels or any combination thereof.

In further embodiments, the compositions of the present invention as compared to placebo or baseline are more potent than other omega-3 compositions known in the prior art (such as LOVAZA®, EPANOVA™ or AMR101) in reducing TG while causing a lesser increase in LDL-cholesterol, a lesser non-significant increase in LDL-cholesterol, no increase in LDL-cholesterol at all, or a more potent reduction in LDL-cholesterol at in patients with baseline TG levels above 500 mg/dL.

In some embodiments, the use of the compositions of the present invention may allow for a reduction in the dose of the statin required for a subject. For example, the coadministration of the composition of the present invention in a subject receiving statin therapy may allow for the reduction of the dose of the statin, compared to subject not being co-administered a composition of the present invention. In some embodiments, the dose of the statin may be reduced by at least 10%, alternatively at least 25%, alternatively at least 50%, or alternatively at least 75%.

In some embodiments, the use of the compositions of the present invention may reduce the time needed for a subject to reach the recommended blood levels. For example, the administration of compositions of the present invention may allow a subject to reach goal lipid levels, for example, those described in the NCEP ATP III Guidelines, or any levels recommended by a health care practitioner. In some embodiments, the reduction of time is greater than 5%, alternatively greater than 15%, alternatively greater than 25%, alternatively greater than 50%, and alternatively greater than 75%.

The compositions of the present invention are also useful to treat coronary heart disease (CHD), vascular disease, atherosclerotic disease or related conditions. The compositions of the present invention may also be use for the treatment and/or prevention and/or reduction of cardiac events and/or cardiovascular events and/or vascular events and/or symptoms. Determination of such cardiovascular diseases/conditions and prevention of events/symptoms in mammals and methods to determine treatment and preventative/therapeutic effects therefore are generally know to those skilled in the art.

The present invention also relates to treatment of such conditions in with concomitant treatments regimes or combination products with other active pharmaceutical ingredients. Such concomitant or fixed combination treatments may include a statin, an anticoagulant (such as aspirin or clopidogrel), an antihypertensive (such as a diuretic, beta-blocker, calcium channel blocker, ACE-inhibitor, angiotensin II receptor (ARB) antagonist), or other treatments for cardiovascular diseases.

The present invention also includes pharmaceutical compositions, for example, a unit dosage, comprising one or more HMG-CoA reductase inhibitors ("statins") and the omega-3 fatty acid composition of the present invention. The present invention may incorporate now known or future known statins in an amount generally recognized as safe. There are currently seven statins that are widely available: atorvastatin, rosuvastatin, fluvastatin, lovastatin, pravastatin, pitavastatin, and simvastatin. An eight statin, cerivastatin, has been removed from the U.S. market at the time of this writing. However, it is conceivable to one skilled in the art that cerivastatin may be used in conjunction with some embodiments of the present invention if cerivastatin is ultimately determined to be safe and effective in certain treatment regimens. Such statins are typically used at their common daily doses, which include, but are not limited to lovastatin 10 mg, 20 mg, 40 mg; pravastatin 10 mg, 20 mg, 40 mg, 80 mg; simvastatin 5 mg, 10 mg, 20 mg, 40 mg, 80 mg; fluvastatin 20 mg, 40 mg, 80 mg; atorvastatin 10 mg, 20 mg, 40 mg, 80 mg; rosuvastatin 5 mg, 10 mg, 20 mg, 40 mg; and pitavastatin 1 mg, 2 mg, 4 mg, 8 mg.

Generally, the effect of statins is dose dependent, i.e., the higher the dose, the greater the therapeutic affect. However, the effect of each statin is different, and therefore the level of therapeutic effect of one statin cannot be necessarily be directly correlated to the level of therapeutic effects of other statins. For example, bioavailability varies widely among the statins. Specifically, it has been shown that simvastatin is less than 5% bioavailable, while fluvastatin is approximately 24% bioavailable. Statins are absorbed at rates ranging from about 30% with lovastatin to 98% with fluvastatin. First-pass metabolism occurs in all statins except pravastatin. Pravastatin is also the least protein-bound of the statins (about 50%), compared with the others, which are more than 90% protein-bound. Accordingly, the statins possess distinct properties from one another. The combination products of this invention involving each statin or a plurality of statins are also distinct.

The present invention also includes methods of treatment, comprising dosing of one or more statins and the omega-3 fatty acid composition of the present invention, either as concomitant therapy or in a fixed dose combination product comprising both a statin and the composition of the present invention. This method of treatment combines the administration of one or more statins at its common dose or an alternative dose with the composition of the present invention.

In some embodiments, the compositions of the present invention, which comprise significant amounts of omega-3 docosapentaenoic acid (DPA-n3) or its glycerol or ethyl esters, together with a common or alternative statin dose, may be used for the treatment of hypertriglyceridemia (either TG≥500 mg/dL, TG≥200 mg/dL, TG≥150 mg/dL, TG 200-499 mg/dL, or TG 150-199 mg/dL), mixed dyslipidemia, or any other diseases or medical conditions specified above. Such methods of treatment provide to a subject in need thereof a dose of at least 30 mg DPA-N3 per day, alternatively at least 40 mg DPA-N3 per day, alternatively at least 50 mg DPA-N3 per day, alternatively at least 60 mg DPA-N3 per day, alternatively at least 70 mg DPA-N3 per day, alternatively at least 80 mg DPA-N3 per day, alternatively at least 90 mg DPA-N3 per day, alternatively at least 100 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 or its glycerol or ethyl esters per day together with a common or alternative statin dose.

In other embodiments, the compositions of the present invention, which comprise significant amounts of omega-3 docosapentaenoic acid (DPA-n3) or its glycerol or ethyl esters and which comprise relatively small amounts of omega-3 docosahexaenoic acid (DHA-n3), together with a common or alternative statin dose, may be used for the treatment of hypertriglyceridemia (either TG≥500 mg/dL, TG≥200 mg/dL, TG≥150 mg/dL, TG 200-499 mg/dL, or TG 150-199 mg/dL), mixed dyslipidemia, or any other diseases or medical conditions specified above. Such method of treatment provides to a subject in need thereof a common or alternative statin dose together with a dose of at least 30 mg DPA-N3 per day, alternatively at least 40 mg DPA-N3 per day, alternatively at least 50 mg DPA-N3 per day, alternatively at least 60 mg DPA-N3 per day, alternatively at least 80 mg DPA-N3 per day, alternatively at least 90 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 or its glycerol or ethyl esters per day, while providing less than 2000 mg of DHA, alternatively less than 1900 mg of DHA, alternatively less than 1500 mg of DHA, alternatively less than 1200 mg of DHA, alternatively less than 1000 mg of DHA, alternatively less than 800 mg of DHA, alternatively less than 700 mg of DHA, alternatively less than 600 mg of DHA, alternatively less than 500 mg of DHA, alternatively less than 400 mg of DHA, alternatively less than 350 mg of DHA, alternatively less than 300 mg of DHA, alternatively less than 250 mg of DHA, alternatively less than 200 mg of DHA, alternatively less than 150 mg of DHA, alternatively less than 120 mg of DHA, alternatively less than 100 mg of DHA, alternatively less than 80 mg of DHA, alternatively less than 60 mg of DHA, alternatively less than 50 mg of DHA, alternatively less than 40 mg of DHA, alternatively less than 30 mg of DHA, alternatively less than 25 mg of DHA, alternatively less than 20 mg of DHA or its glycerol or ethyl esters per day.

In further embodiments, the compositions of the present invention, which comprise significant amounts of omega-3 docosapentaenoic acid (DPA-n3) or its glycerol or ethyl esters and which comprise relatively small amounts of omega-3 docosahexaenoic acid (DHA-n3), together with a common or alternative statin dose, may be used for the treatment of hypertriglyceridemia (either TG≥500 mg/dL, TG≥200 mg/dL, TG≥150 mg/dL, TG 200-499 mg/dL, or TG 150-199 mg/dL), mixed dyslipidemia, or any other diseases or medical conditions specified above. Such method of treatment provides to a subject in need thereof a common or alternative statin dose together with a dose of at least 30 mg DPA-N3 per day, alternatively at least 40 mg DPA-N3 per day, alternatively at least 50 mg DPA-N3 per day, alternatively at least 60 mg DPA-N3 per day, alternatively at least 70 mg DPA-N3 per day, alternatively at least 80 mg DPA-N3 per day, alternatively at least 90 mg DPA-N3 per day, alternatively at least 100 mg DPA-N3 per day, alternatively at least 120 mg DPA-N3 per day, alternatively at least 150 mg DPA-N3 per day, alternatively at least 160 mg DPA-N3 per day, alternatively at least 180 mg DPA-N3 per day, alternatively at least 200 mg DPA-N3 per day, alternatively at least 250 mg DPA-N3 per day, alternatively at least 300 mg DPA-N3 per day, alternatively at least 350 mg DPA-N3 per day, alternatively at least 400 mg DPA-N3 per day, alternatively at least 500 mg DPA-N3 per day, alternatively at least 600 mg DPA-N3 per day, alternatively at least 800 mg DPA-N3 per day, alternatively at least 1000 mg DPA-N3 per day, alternatively at least 1200 mg DPA-N3 per day, alternatively at least 1500 mg DPA-N3 or its glycerol or ethyl esters per day, while providing a relatively small amount of DHA-N3 such that the DHA:DPA dose ratio is no more than 15:1 of DHA:DPA, alternatively no more than 12:1 of DHA:DPA, alternatively no more than 10:1 of DHA:DPA, alternatively no more than 8:1 of DHA:DPA, alternatively no more than 5:1 of DHA:DPA, alternatively no more than 3:1 of DHA:DPA, alternatively no more than 2:1 of DHA:DPA, alternatively no more than 1:1 of DHA:DPA, alternatively no more than 1:2 of DHA:DPA, alternatively no more than 1:3 of DHA:DPA, alternatively no more than 1:5 of DHA:DPA, alternatively no more than 1:8 of DHA:DPA, alternatively no more than 1:10 of DHA:DPA, alternatively no more than 1:15 of DHA:DPA, alternatively a relative daily dose of no more than 1:20 of DHA:DPA.

In some embodiments, the composition of the present invention further comprises TPA at concentration of at least 0.05%. In some embodiments, the TPA concentration is about 0.01% to about 5%, alternatively about 0.05% to about 2%, alternatively about 0.1% to about 1%, alternatively about 0.2% to about 0.8%, alternatively about 0.4% to about 0.6%, alternatively about 0.5%.

The compositions of the present invention may also be taken as a general nutritional supplement.

On a EPA+DPA daily dose basis, the compositions of the present invention are preferably provided in a dose of between 100 mg and 10,100 mg/day, alternatively between 200 mg and 8,100 mg/day, alternatively between 300 mg and 6,100 mg/day, alternatively between 400 mg and 5,100 mg/day, alternatively between 500 mg and 4,100 mg/day.

On a EPA+HPA+DPA daily dose basis, the compositions of the present invention are preferably provided in a dose of between 100 mg and 10,100 mg/day, alternatively between 200 mg and 8,100 mg/day, alternatively between 300 mg and 6,100 mg/day, alternatively between 400 mg and 5,100 mg/day, alternatively between 500 mg and 4,100 mg/day.

The formulation may be a single daily dose preparation to give in one dose the above intakes, or may be in convenient divided doses, for example, a daily dose formed of two to four soft gelatin or other dosage forms, each containing 300-1500 mg of EPA+DPA or EPA+DPA+HPA in any form embodied in the present invention.

Flavourants or emulsifiers may be included, for instance, to make the preparation palatable. Other conventional additives, diluents and excipients may be present. The preparation for ingestion may be in the form of a capsule, a dry powder, a tablet, a solution, an oil, an emulsion or any other appropriate form. The capsules may be hard or soft gelatin capsules, agar capsules, or any other appropriate capsule.

Use of the formulations of the invention in the manufacture of a medicament for the treatment or prevention of any disease or disorder, including those mentioned above, is included in the present invention.

The omega-3 fatty acid composition optionally includes chemical antioxidants, such as alpha tocopherol, which are administered in pure form or suspended in a vegetable oil, such as soybean oil or corn oil.

The blended fatty acid compositions may then be incorporated into any appropriate dosage form for oral, enteral, parenteral, rectal, vaginal, dermal or other route of administration. Soft or hard gelatin capsules, flavoured oil blends, emulsifiers or other liquid forms, and microencapsulate powders or other dry form vehicles are all appropriate ways of administering the products.

The formulated final drug product containing the omega-3 fatty acid composition may be administered to a mammal or patient in need thereof in a capsule, a tablet, a powder that can be dispersed in a beverage, or another solid oral dosage form, a liquid, a soft gel capsule or other convenient dosage form such as oral liquid in a capsule, as known in the art. In some embodiments, the capsule comprises a hard gelatin. The combination product may also be contained in a liquid suitable for injection or infusion.

Example pharmaceutical grade finished dosage forms: (a) Soft or hard gelatin capsules each containing 500 mg or 1000 mg of a mix 20 parts of EPA as a free fatty acid to 1 parts of DPA as a free fatty acid; (b) As in (a) but where the EPA and DPA free fatty acids are replaced with the fatty acids in any other appropriate bioassimilable form such as the ethyl esters; (c) As in (a)-(b) but where the material is in the form of a microencapsulated powder which can be used as a powder or compressed into tablets. Such powders may be prepared by a variety of technologies known to those skilled in the art; (d) As in (a)-(b) but where the formulation is a liquid or emulsion, appropriately flavoured for palatable oral administration; (e) As in (a)-(b) but where the material is formulated into a pharmaceutically acceptable vehicle appropriate for topical application such as a cream or ointment.

The omega-3 compositions of the present invention may also be administered with a combination of one or more non-active pharmaceutical ingredients (also known generally herein as "excipients"). Non-active ingredients, for example, serve to solubilize, suspend, thicken, dilute, emulsify, stabilize, preserve, protect, color, flavor, and fashion the active ingredients into an applicable and efficacious preparation that is safe, convenient, and otherwise acceptable for use. Thus, the non-active ingredients may include colloidal silicon dioxide, crospovidone, lactose monohydrate, lecithin, microcrystalline cellulose, polyvinyl alcohol, povidone, sodium lauryl sulfate, sodium stearyl fumarate, talc, titanium dioxide and xanthum gum.

The term "pharmaceutically acceptable vehicle," as used herein, includes any of the following: a solution where the first API and optional other ingredients are wholly dissolved in a solubilizer (e.g., a pharmaceutically acceptable solvent or mixture of solvents), wherein the solution remains in clear liquid form at about room temperature; a suspension; an oil; or a semi-solid, wherein the first API and optionally other ingredients are dissolved wholly or partially in a solubilizer (an emulsion, cream, etc.).

A "pharmaceutical grade finished dosage form" as used herein may be construed as a unit dose form suitable for administration to, for example, human or animal subjects, and having content uniformity acceptable to regulatory authorities. For example, under the USP requirements for content uniformity, a pharmaceutical grade finished dosage form should have an amount of API within the range of 85% to 115% of the desired dosage and an RSD less than or equal to 6.0%. In addition, a pharmaceutical grade finished dosage form must be stable (i.e., have a "shelf life") for a pharmaceutically acceptable duration of time, preferably at least six months, alternatively at least one year, or at least two years, when stored at room temperature (about 23 degree Celcius to 27 degree Celcius, preferably about 25 degree Celcius) and 60% relative humidity. Typically, stability is determined by physical appearance and/or chemical modification of the ingredients, in accordance with standards well-known in the pharmaceutical arts, including those documented in ICH guidelines.

The omega-3 fatty acid dosage form optionally includes chemical antioxidants, such as alpha tocopherol, oils, such as soybean oil and partially hydrogenated vegetable oil, and lubricants such as fractionated coconut oil, lecithin and a mixture of the same.

EXAMPLES

Example 1

A composition according to the present prevention is prepared by mixing and homogenizing in a ratio of 98:2 the intermediates MEGAPEX E90D00EE (90% EPA ethyl ester) and MAXOMEGA DPA95 FFA (≥95% DPA synthetic fatty acid produced from EPA ethyl ester concentrate) converted to ethyl ester, respectively. These intermediates were prepared and commercially offered for sale by Chemport Korea (MEGAPEX) and Equateq Ltd from Scotland, UK (MAXOMEGA). The relative amounts of fatty acids present in the starting intermediates and in the resulting novel composition are listed in Table 1 below. The resulting novel composition comprises 89.10% EPA, 1.95% DPA, 0.19% HPA, 91.24% omega-3-pentaenoic acids, less than 0.01% DHA, 91.24% omega-3-pentaenoic acids, 93.09% total omega-3 fatty acids, 3.15% ARA and 3.57% omega-6 fatty acids (all Area %).

TABLE 1

Fatty acid Composition (Area %) of intermediates and novel composition according to Example 1

| Fatty Acid | 98.0% Megapex E90D00EE | 2.0% Maxomega DPA95FFA => EE | Novel Composition |
|---|---|---|---|
| c18:0 | 0.05 | 0 | 0.05 |
| c18:1n9 | 0.06 | 0 | 0.06 |
| c18:1n7 | 0.02 | 0 | 0.02 |
| c18:2n6 | 0.01 | 0 | 0.01 |
| c18:3n6 | 0.02 | 0 | 0.02 |
| c18:3n3 | 0.03 | 0 | 0.03 |
| c18:4n3 | 0.42 | 0 | 0.41 |
| c18:4n1 | 0.07 | 0 | 0.07 |
| c20:0 | 0 | 0 | 0.00 |
| c20:1n11 | 0 | 0 | 0.00 |
| c20:1n9 | 0 | 0 | 0.00 |
| c20:1n7 | 0 | 0 | 0.00 |
| c20:2n6 | 0.25 | 0 | 0.25 |
| c20:3n9 | 0 | 0 | 0.00 |
| c20:3n6 | 0.15 | 0 | 0.15 |
| c21:0 | 0 | 0 | 0.00 |
| c20:4n6 | 3.21 | 0 | 3.15 |
| c20:3n3 | 0 | 0 | 0.00 |
| c20:4n3 | 1.44 | 0 | 1.41 |
| c20:5n3 | 90.92 | 0 | 89.10 |
| c22:0 | 0.3 | 0 | 0.29 |
| c22:1n11 | 0.07 | 0 | 0.07 |
| c22:1n9 | 0.18 | 0 | 0.18 |
| c22:1n7 | 0.19 | 0 | 0.19 |
| c21:5n3 | 0.19 | 0 | 0.19 |
| c22:5n6 | 0 | 0 | 0.00 |
| c22:5n3 | 0 | 97.27 | 1.95 |
| c22:6n3 | 0 | 0 | 0.00 |
| c24:0 | 0 | 0.33 | 0.01 |
| OTHER | 2.42 | 2.4 | 2.42 |
| | 100 | 100 | 100 |

Example 2

A composition according to the present prevention is prepared by mixing and homogenizing in a ratio of 96:4 the intermediates MEGAPEX E90D00EE (90% EPA ethyl ester) and MAXOMEGA DPA95 FFA (≥95% DPA synthetic fatty acid produced from EPA ethyl ester concentrate), converted to ethyl ester, respectively. These intermediates were prepared and commercially offered for sale by Chemport Korea (MEGAPEX) and Equateq Ltd from Scotland, UK (MAXOMEGA). The relative amounts of fatty acids present in the starting intermediates and in the resulting novel composition is listed in Table 2 below. The resulting novel composition comprises 87.28% EPA, 3.89% DPA, 0.18% HPA, 91.35% omega-3-pentaenoic acids, less than 0.01% DHA, 93.17% total omega-3 fatty acids and 3.49% omega-6 fatty acids (all Area %).

TABLE 2

Fatty acid Composition (Area %) of intermediates and novel composition according to Example 2

| Fatty Acid | 96.0% Megapex E90D00EE | 4.0% Maxomega DPA95FFA => EE | Novel Composition |
|---|---|---|---|
| c18:0 | 0.05 | 0 | 0.05 |
| c18:1n9 | 0.06 | 0 | 0.06 |
| c18:1n7 | 0.02 | 0 | 0.02 |
| c18:2n6 | 0.01 | 0 | 0.01 |
| c18:3n6 | 0.02 | 0 | 0.02 |
| c18:3n3 | 0.03 | 0 | 0.03 |
| c18:4n3 | 0.42 | 0 | 0.40 |
| c18:4n1 | 0.07 | 0 | 0.07 |
| c20:0 | 0 | 0 | 0.00 |
| c20:1n11 | 0 | 0 | 0.00 |
| c20:1n9 | 0 | 0 | 0.00 |
| c20:1n7 | 0 | 0 | 0.00 |
| c20:2n6 | 0.25 | 0 | 0.24 |
| c20:3n9 | 0 | 0 | 0.00 |
| c20:3n6 | 0.15 | 0 | 0.14 |
| c21:0 | 0 | 0 | 0.00 |
| c20:4n6 | 3.21 | 0 | 3.08 |
| c20:3n3 | 0 | 0 | 0.00 |
| c20:4n3 | 1.44 | 0 | 1.38 |
| c20:5n3 | 90.92 | 0 | 87.28 |
| c22:0 | 0.3 | 0 | 0.29 |
| c22:1n11 | 0.07 | 0 | 0.07 |
| c22:1n9 | 0.18 | 0 | 0.17 |
| c22:1n7 | 0.19 | 0 | 0.18 |
| c21:5n3 | 0.19 | 0 | 0.18 |
| c22:5n6 | 0 | 0 | 0.00 |
| c22:5n3 | 0 | 97.27 | 3.89 |
| c22:6n3 | 0 | 0 | 0.00 |
| c24:0 | 0 | 0.33 | 0.01 |
| OTHER | 2.42 | 2.4 | 2.42 |
| | 100 | 100 | 100 |

Example 3

A composition according to the present prevention is prepared by mixing and homogenizing in a ratio of 94:6 the intermediates MEGAPEX E90D00EE (90% EPA ethyl ester) and MAXOMEGA DPA95 FFA (≥95% DPA synthetic fatty acid produced from EPA ethyl ester concentrate) converted to ethyl ester, respectively. These intermediates were prepared and commercially offered for sale by Chemport Korea (MEGAPEX) and Equateq Ltd from Scotland, UK (MAXOMEGA). The relative amounts of fatty acids present in the starting intermediates and in the resulting novel composition are listed in table 3 below. The resulting novel composition comprises 85.46% EPA, 5.84% DPA, 0.18% HPA, 91.48% omega-3-pentaenoic acids, less than 0.01% DHA, 93.26% total omega-3 fatty acids, 3.02% ARA, and 3.42% omega-6 fatty acids (all Area %).

TABLE 3

Fatty acid Composition (Area %) of intermediates and novel composition according to Example 3

| Fatty Acid | 94.0% Megapex E90D00EE | 6.0% Maxomega DPA95FFA => EE | Novel Composition |
|---|---|---|---|
| c18:0 | 0.05 | 0 | 0.05 |
| c18:1n9 | 0.06 | 0 | 0.06 |
| c18:1n7 | 0.02 | 0 | 0.02 |
| c18:2n6 | 0.01 | 0 | 0.01 |
| c18:3n6 | 0.02 | 0 | 0.02 |
| c18:3n3 | 0.03 | 0 | 0.03 |
| c18:4n3 | 0.42 | 0 | 0.39 |
| c18:4n1 | 0.07 | 0 | 0.07 |
| c20:0 | 0 | 0 | 0.00 |
| c20:1n11 | 0 | 0 | 0.00 |
| c20:1n9 | 0 | 0 | 0.00 |
| c20:1n7 | 0 | 0 | 0.00 |

TABLE 3-continued

Fatty acid Composition (Area %) of intermediates
and novel composition according to Example 3

| Fatty Acid | 94.0% Megapex E90D00EE | 6.0% Maxomega DPA95FFA => EE | Novel Composition |
|---|---|---|---|
| c20:2n6 | 0.25 | 0 | 0.24 |
| c20:3n9 | 0 | 0 | 0.00 |
| c20:3n6 | 0.15 | 0 | 0.14 |
| c21:0 | 0 | 0 | 0.00 |
| c20:4n6 | 3.21 | 0 | 3.02 |
| c20:3n3 | 0 | 0 | 0.00 |
| c20:4n3 | 1.44 | 0 | 1.35 |
| c20:5n3 | 90.92 | 0 | 85.46 |
| c22:0 | 0.3 | 0 | 0.28 |
| c22:1n11 | 0.07 | 0 | 0.07 |
| c22:1n9 | 0.18 | 0 | 0.17 |
| c22:1n7 | 0.19 | 0 | 0.18 |
| c21:5n3 | 0.19 | 0 | 0.18 |
| c22:5n6 | 0 | 0 | 0.00 |
| c22:5n3 | 0 | 97.27 | 5.84 |
| c22:6n3 | 0 | 0 | 0.00 |
| c24:0 | 0 | 0.33 | 0.02 |
| OTHER | 2.42 | 2.4 | 2.42 |
|  | 100 | 100 | 100 |

Example 4

A composition according to the present prevention is prepared by mixing and homogenizing in a ratio of 75:25 the intermediates MEGAPEX E90D00EE (90% EPA ethyl ester) and MAXOMEGA DPA95 FFA (≥95% DPA synthetic fatty acid produced from EPA ethyl ester concentrate, converted to ethyl ester, respectively. These intermediates were prepared and commercially offered for sale by Chemport Korea (MEGAPEX) and Equateq Ltd from Scotland, UK (MAXOMEGA). The relative amounts of fatty acids present in the starting intermediates and in the resulting novel composition is listed in table 4 below. The resulting novel composition comprises 68.10% EPA, 24.32% DPA, 0.19% HPA, 92.65% omega-3-pentaenoic acids, less than 0.01% DHA, 94.07% total omega-3 fatty acids, 2.41% ARA and 2.73% omega-6 fatty acids (all Area %).

TABLE 4

Fatty acid Composition (Area %) of intermediates
and novel composition according to Example 4

| Fatty Acid | 75.0% Megapex E90D00EE | 25.0% Maxomega DPA95FFA => EE | Novel Composition |
|---|---|---|---|
| c18:0 | 0.05 | 0 | 0.04 |
| c18:1n9 | 0.06 | 0 | 0.05 |
| c18:1n7 | 0.02 | 0 | 0.02 |
| c18:2n6 | 0.01 | 0 | 0.01 |
| c18:3n6 | 0.02 | 0 | 0.02 |
| c18:3n3 | 0.03 | 0 | 0.02 |
| c18:4n3 | 0.42 | 0 | 0.32 |
| c18:4n1 | 0.07 | 0 | 0.05 |
| c20:0 | 0 | 0 | 0.00 |
| c20:1n11 | 0 | 0 | 0.00 |
| c20:1n9 | 0 | 0 | 0.00 |
| c20:1n7 | 0 | 0 | 0.00 |
| c20:2n6 | 0.25 | 0 | 0.19 |
| c20:3n9 | 0 | 0 | 0.00 |
| c20:3n6 | 0.15 | 0 | 0.11 |
| c21:0 | 0 | 0 | 0.00 |
| c20:4n6 | 3.21 | 0 | 2.41 |
| c20:3n3 | 0 | 0 | 0.00 |

TABLE 4-continued

Fatty acid Composition (Area %) of intermediates
and novel composition according to Example 4

| Fatty Acid | 75.0% Megapex E90D00EE | 25.0% Maxomega DPA95FFA => EE | Novel Composition |
|---|---|---|---|
| c20:4n3 | 1.44 | 0 | 1.08 |
| c20:5n3 | 90.92 | 0 | 68.19 |
| c22:0 | 0.3 | 0 | 0.23 |
| c22:1n11 | 0.07 | 0 | 0.05 |
| c22:1n9 | 0.18 | 0 | 0.14 |
| c22:1n7 | 0.19 | 0 | 0.14 |
| c21:5n3 | 0.19 | 0 | 0.14 |
| c22:5n6 | 0 | 0 | 0.00 |
| c22:5n3 | 0 | 97.27 | 24.32 |
| c22:6n3 | 0 | 0 | 0.00 |
| c24:0 | 0 | 0.33 | 0.08 |
| OTHER | 2.42 | 2.4 | 2.42 |
|  | 100 | 100 | 100 |

Example 5

A composition according to the present prevention is prepared by mixing and homogenizing in a ratio of 60:40 the intermediates KD-PharmaKD-PUR 900EE and MAXOMEGA DPA95 FFA converted to ethyl ester, respectively. These intermediates were prepared and commercially offered for sale by KD-Pharma Germany (KD-Pharma) and Equateq Ltd from Scotland, UK (MAXOMEGA). The relative amounts of fatty acids present in the starting intermediates and in the resulting novel composition is listed in table 5 below. The resulting novel composition comprises 55.74% EPA, 39.26% DPA, 2.39% HPA, 97.44% omega-3-pentaenoic acids, and 98.06% total omega-3 fatty acids (all Area %).

TABLE 5

Fatty acid Composition (Area %) of intermediates
and novel composition according to Example 5

| Fatty Acid | 60.0% KD-Pur 900EE | 40.0% Maxomega DPA95FFA => EE | Novel Composition |
|---|---|---|---|
| c18:0 | 0 | 0 | 0.00 |
| c18:1n9 | 0 | 0 | 0.00 |
| c18:1n7 | 0 | 0 | 0.00 |
| c18:2n6 | 0 | 0 | 0.00 |
| c18:3n6 | 0 | 0 | 0.00 |
| c18:3n3 | 0 | 0 | 0.00 |
| c18:4n3 | 0 | 0 | 0.00 |
| c18:4n1 | 0 | 0 | 0.00 |
| c20:0 | 0 | 0 | 0.00 |
| c20:1n11 | 0 | 0 | 0.00 |
| c20:1n9 | 0 | 0 | 0.00 |
| c20:1n7 | 0 | 0 | 0.00 |
| c20:2n6 | 0 | 0 | 0.00 |
| c20:3n9 | 0 | 0 | 0.00 |
| c20:3n6 | 0 | 0 | 0.00 |
| c21:0 | 0 | 0 | 0.00 |
| c20:4n6 | 0 | 0 | 0.00 |
| c20:3n3 | 0 | 0 | 0.00 |
| c20:4n3 | 1.04 | 0 | 0.62 |
| c20:5n3 | 92.99 | 0 | 55.79 |
| c22:0 | 0 | 0 | 0.00 |
| c22:1n11 | 0 | 0 | 0.00 |
| c22:1n9 | 0 | 0 | 0.00 |
| c22:1n7 | 0 | 0 | 0.00 |
| c21:5n3 | 3.98 | 0 | 2.39 |
| c22:5n6 | 0 | 0 | 0.00 |
| c22:5n3 | 0.58 | 97.27 | 39.26 |

TABLE 5-continued

Fatty acid Composition (Area %) of intermediates and novel composition according to Example 5

| Fatty Acid | 60.0% KD-Pur 900EE | 40.0% Maxomega DPA95FFA => EE | Novel Composition |
|---|---|---|---|
| c22:6n3 | 0 | 0 | 0.00 |
| c24:0 | 0 | 0.33 | 0.13 |
| OTHER | 1.41 | 2.4 | 1.81 |
| | 100.00 | 100 | 100.00 |

Example 6

A composition according to the present prevention is prepared by mixing and homogenizing in a ratio of 96:4 the intermediates KD-PUR 900EE KD-Pharma and MAX-OMEGA DPA95 FFA converted to ethyl ester, respectively. These intermediates were prepared and commercially offered for sale by KD-Pharma Germany (KD-Pharma) and Equateq Ltd from Scotland, UK (MAXOMEGA). The relative amounts of fatty acids present in the starting intermediates and in the resulting novel composition is listed in table 6 below. The resulting novel composition comprises 89.27% EPA, 4.45% DPA, 3.82% HPA, 97.54% omega-3-pentaenoic acids, and 98.54% total omega-3 fatty acids (all Area %).

TABLE 6

Fatty acid Composition (Area %) of intermediates and novel composition according to Example 6

| Fatty Acid | 96.0% KD-Pur 900EE | 4.0% Maxomega DPA95FFA => EE | Novel Composition |
|---|---|---|---|
| c18:0 | 0 | 0 | 0.00 |
| c18:1n9 | 0 | 0 | 0.00 |
| c18:1n7 | 0 | 0 | 0.00 |
| c18:2n6 | 0 | 0 | 0.00 |
| c18:3n6 | 0 | 0 | 0.00 |
| c18:3n3 | 0 | 0 | 0.00 |
| c18:4n3 | 0 | 0 | 0.00 |
| c18:4n1 | 0 | 0 | 0.00 |
| c20:0 | 0 | 0 | 0.00 |
| c20:1n11 | 0 | 0 | 0.00 |
| c20:1n9 | 0 | 0 | 0.00 |
| c20:1n7 | 0 | 0 | 0.00 |
| c20:2n6 | 0 | 0 | 0.00 |
| c20:3n9 | 0 | 0 | 0.00 |
| c20:3n6 | 0 | 0 | 0.00 |
| c21:0 | 0 | 0 | 0.00 |
| c20:4n6 | 0 | 0 | 0.00 |
| c20:3n3 | 0 | 0 | 0.00 |
| c20:4n3 | 1.04 | 0 | 1.00 |
| c20:5n3 | 92.99 | 0 | 89.27 |
| c22:0 | 0 | 0 | 0.00 |
| c22:1n11 | 0 | 0 | 0.00 |
| c22:1n9 | 0 | 0 | 0.00 |
| c22:1n7 | 0 | 0 | 0.00 |
| c21:5n3 | 3.98 | 0 | 3.82 |
| c22:5n6 | 0 | 0 | 0.00 |
| c22:5n3 | 0.58 | 97.27 | 4.45 |
| c22:6n3 | 0 | 0 | 0.00 |
| c24:0 | 0 | 0.33 | 0.01 |
| OTHER | 1.41 | 2.4 | 1.45 |
| | 100.00 | 100 | 100.00 |

Example 7

The ethyl ester composition of Example 4 may be converted into a free fatty acid composition with essentially the same fatty acid composition according to "Conversion Method EE to FFA" below. This method is indiscriminate with respect to the type, degree of saturation or length of fatty acid if performed for an adequate amount of time under the described conditions.

Conversion Method EE to FFA
1. Fatty Acid Ethyl Ester (FAEE GMP, approx. 3 mmol/g) oil is brought into a closed heated/cooled reaction chamber under nitrogen atmosphere (preferably with pressure control), and heated to 50-60 degree Celcius under stirring.
2. 2M NaOH solution in water is added under firm stirring to ensure phase mixing (est. 2-3×FAEE w/w) and stir until no ethyl ester is presence (est. 2-4 hrs). Test ethyl ester presence at lab scale/in process with TLC (hexanes/EtOAc 9:1) and with EP GC method to confirm reaction completion under GMP.
3. Under cooling (keep mixture below 70 degree Celcius), add 6M HCl in water (est. <1 hr) until slightly acid (~pH3-4). It may be necessary to control pressure to prevent excessive foaming. Then halt stirring, give time to let phases separate, and remove water phase from bottom (keep oil protected from oxygen, apply nitrogen atmosphere blanket).
4. Add demineralized water (est. 2-3×FAEE w/w) and wash out NaCl and ethanol from oil under firm stirring (est. ~1 hr). Halt stirring, give time to let phases separate, and remove water phase from bottom (keep oil protected from oxygen, apply nitrogen atmosphere blanket).
5. Repeat Step 4 several times (~2×) to remove ethanol and NaCl.
6. Remove water and remaining ethanol [determine in-process controls], confirm under GMP with USP residual solvent method (target: ethanol <100 ppm) by stirring oil while applying vacuum 10-50 mbar (with solvent trap) and heat oil (70-80 degree celcius) until water/ethanol target is met (est. 2-4 hrs).
7. Add anti-oxidants (i.e. alpha-D-tocopherol, USP, target 4 mg/g) and/or other excipients.
8. All reagents and excipients USP grade.

Example 8

The ethyl ester composition of Example 3 is converted into a free fatty acid composition with essentially the same fatty acid composition according to "Conversion Method EE to FFA" above. This method is indiscriminate with respect to the type, degree of saturation or length of fatty acid if performed for an adequate amount of time under the described conditions.

Example 9

The ethyl ester composition of Example 6 is converted into a free fatty acid composition with essentially the same fatty acid composition according to "Conversion Method EE to FFA" above. This method is indiscriminate with respect to the type, degree of saturation or length of fatty acid if performed for an adequate amount of time under the described conditions.

Example 10

The composition of Example 4 is formulated into a soft gelatin capsule. Prior to encapsulation, an anti-oxidant preparation (composed of 4000 mg alpha-D-tocopherol in one liter of corn oil; corn oil is a triglyceride low in omega-3) is added to the composition of Example 4, by mixing and homogenizing 100 mL of this anti-oxidant preparation into 100 liters of the oil composition of Example 4 followed by thorough homogenization. The resulting pre-encapsulation formulated oil contains approximately 4 mg/gram alpha-D-tocopherol. Subsequently, the formulated oil is encapsulated into soft gelatin capsules with printed logo according to general methods typically used by Accucaps in Canada for fish oils or by any other documented and operational encapsulation method. The fill mass of the oil is approximately 1.08 gram/capsule, providing a dose of approximately 1000 mg omega-3-pentaenoic-acids ethyl esters per capsule. Finally, the capsules are bottled in HDPE bottles with induction seal and child resistant cap.

Example 11

The composition of Example 8 is formulated into a soft gelatin capsule. Prior to encapsulation, an anti-oxidant preparation (composed of 4000 mg alpha-D-tocopherol in one liter of corn oil; corn oil is a triglyceride low in omega-3) is added to the composition of Example 4, by mixing and homogenizing 100 mL of this anti-oxidant preparation into 100 liters of the oil composition of Example 4 followed by thorough homogenization. The resulting pre-encapsulation formulated oil contains approximately 4 mg/gram alpha-D-tocopherol. Subsequently, the formulated oil is encapsulated into soft gelatin capsules with printed logo according to general methods typically used by Banner in High Point, N.C., for fish oils or by any other documented and operational encapsulation method. The fill mass of the oil is approximately 1.09 gram/capsule, providing a dose of approximately 1000 mg omega-3-pentaenoic-acids per capsule. Finally, the capsules are bottled in HDPE bottles with induction seal and child resistant cap.

Example 12

The composition of Example 5 is formulated into a soft gelatin capsule. Prior to encapsulation, an anti-oxidant preparation (composed of 4000 mg alpha-D-tocopherol in one liter of corn oil; corn oil is a triglyceride low in omega-3) is added to the composition of Example 4, by mixing and homogenizing 100 mL of this anti-oxidant preparation into 100 liters of the oil composition of Example 4 followed by thorough homogenization. The resulting pre-encapsulation formulated oil contains approximately 4 mg/gram alpha-D-tocopherol. Subsequently, the formulated oil is encapsulated into soft gelatin capsules with printed logo according to general methods typically used by Catalent in St. Petersburg, Fla., for fish oils or by any other documented and operational encapsulation method. The fill mass of the oil is approximately 1.05 gram/capsule, providing a dose of approximately 1000 mg omega-3-pentaenoic-acids ethyl esters per capsule. Finally, the capsules are bottled in HDPE bottles with induction seal and child resistant cap.

Example 13

The composition of Example 9 is formulated into a soft gelatin capsule. Prior to encapsulation, an anti-oxidant preparation (composed of 4000 mg alpha-D-tocopherol in one liter of corn oil; corn oil is a triglyceride low in omega-3) is added to the composition of Example 4, by mixing and homogenizing 100 mL of this anti-oxidant preparation into 100 liters of the oil composition of Example 4 followed by thorough homogenization. The resulting pre-encapsulation formulated oil contains approximately 4 mg/gram alpha-D-tocopherol. Subsequently, the formulated oil is encapsulated into soft gelatin capsules with printed logo according to general methods typically used by Banner in High Point, N.C., for fish oils or by any other documented and operational encapsulation method. The fill mass of the oil is 1.06 gram/capsule, providing a dose of approximately 1000 mg omega-3-pentaenoic-acids per capsule. Finally, the capsules are bottled in HDPE bottles with induction seal and child resistant cap.

Example 14

A patient is diagnosed with severe hypertriglyceridemia (TG>500 mg/dL). Thereupon, the patient may be initiated on daily treatment with one of the encapsulated compositions according to Examples 10, 11, 12 or 13. Four capsules per day are administered to this patient (4 g/d).

Example 15

A patient is treated as per Example 14. The treatment results in significant reduction of TG as well as non-HDL- and VLDL-cholesterol levels while the LDL-cholesterol level changes insignificantly.

Example 16

A patient is treated as per Example 14. The treatment results in significant reduction of TG as well as non-HDL-, LDL- and VLDL-cholesterol levels.

Example 17

A patient already undergoing treatment with a statin is diagnosed with high triglycerides (TG between 200 and 500 mg/dL). Thereupon, the patient is initiated on daily treatment with one of the encapsulated compositions according to Examples 10, 11, 12 or 13. Four capsules per day are administered to this patient (4 g/d).

Example 18

A patient is treated as per Example 17. The treatment results in significant reduction of TG as well as non-HDL-, VLDL- and LDL-cholesterol levels.

Example 19

A patient is diagnosed with mixed dyslipidemia (TG between 200 and 700 mg/dL and LDL-cholesterol above 190 mg/dL). Thereupon, the patient is initiated on concomitant daily treatment with a statin and one of the encapsulated compositions according to Examples 10, 11, 12 or 13. Four capsules per day are administered to this patient (4 g/d).

Example 20

A patient is treated as per Example 19. The treatment results in significant reduction of TG as well as non-HDL-, VLDL- and LDL-cholesterol levels.

Example 21

A patient is diagnosed with mixed dyslipidemia (TG between 200 and 700 mg/dL and non-HDL-cholesterol above 200 mg/dL). Thereupon, the patient is initiated on concomitant daily treatment with a statin and one of the encapsulated compositions according to Examples 10, 11, 12 or 13. Four capsules per day are administered to this patient (4 g/d).

Example 22

A patient is treated as per Example 21. The treatment results in significant reduction of TG as well as non-HDL-, VLDL- and LDL-cholesterol levels.

Example 23

A patient is diagnosed to be at significant risk for a cardiovascular event according to the NCEP guidelines and has TG levels above 150 mg/dL. Thereupon, the patient is initiated on daily treatment with one of the encapsulated compositions according to Examples 10, 11, 12 or 13. Four capsules per day are administered to this patient (4 g/d).

Example 24

A patient is treated as per Example 23. The treatment results in significant reduction of TG as well as non-HDL-, VLDL- and LDL-cholesterol levels.

Example 25

A patient diagnosed as per Example 14, 17, 19, 21 or 23 is treated with 3 capsules per day (instead of 4) of one of the encapsulated compositions according to Examples 10, 11, 12 or 13. The treatment results in significant reduction of TG as well as non-HDL- and VLDL-cholesterol levels.

Example 26

A patient diagnosed as per Example 14, 17, 19, 21 or 23 is treated with 3 capsules per day (instead of 4) of one of the encapsulated compositions according to Examples 10, 11, 12 or 13. The treatment results in significant reduction of TG as well as non-HDL-, VLDL- and LDL-cholesterol levels.

Example 27

A patient diagnosed as per Example 14, 17, 19, 21 or 23 is treated with 2 capsules per day (instead of 3 or 4) of one of the encapsulated compositions according to Examples 10, 11, 12 or 13. The treatment results in significant reduction of TG as well as non-HDL- and VLDL-cholesterol levels.

Example 28

A patient diagnosed as per Example 14, 17, 19, 21 or 23 is treated with 2 capsules per day (instead of 3 or 4) of one of the encapsulated compositions according to Examples 10, 11, 12 or 13. The treatment results in significant reduction of TG as well as non-HDL-, VLDL- and LDL-cholesterol levels.

Example 29

The following is an example of an embodiment of the present invention.

| COMPOSITION 1 | | | |
|---|---|---|---|
| Composition | Minimum (mg/g) | Maximum (mg/g) | Target (mg/g) |
| Omega-3 pentaenoic acid | 870 | 990 | 920 |
| Eicosapentaenoic acid (EPA) | 750 | 950 | 830 |
| Heneicosapentaenoic acid (HPA) | 5 | 70 | 40 |
| Docosapentaenoic acid (DPA) | 50 | 130 | 90 |
| Docosahexaenoic acid (DHA) | | 40 | 20 |

In COMPOSITION 1, the EPA:HPA ratio is between 13 and 190, the EPA:DPA ratio is between 8 and 15, the HPA:DPA ration between 0.05 and 1, the DPA:DHA ratio more than 2.4, preferably more than 4, more preferably more than 6, most preferably more than 10, and the EPA:DHA ratio more than 32, preferably more than 38, more preferably more than 80, most preferably more than 95. The EPA, HPA, DPA and DHA may be composed as a glyceride (such as triglyceride), an ester (such as ethyl ester), or a free fatty acid.

Example 30

The following is an example of an embodiment of the present invention.

| COMPOSITION 2 | | | |
|---|---|---|---|
| Composition | Minimum (mg/g) | Maximum (mg/g) | Target (mg/g) |
| Omega-3 pentaenoic acid | 900 | 980 | 940 |
| Eicosapentaenoic acid (EPA) | 15 | 60 | 30 |
| Heneicosapentaenoic acid (HPA) | 5 | 60 | 30 |
| Docosapentaenoic acid (DPA) | 800 | 950 | 880 |
| Docosahexaenoic acid (DHA) | | 25 | <10 |

In COMPOSITION 2, the EPA:HPA ratio is between 0.25 and 12, the DPA:EPA ratio is between 13 and 63, the DPA:HPA ration between 13 and 190, the DPA:DHA ratio more than 32, preferably more than 38, more preferably more than 80, most preferably more than 95, and the EPA:DHA ratio more than 00.6, preferably more than 1.5, more preferably more than 2.4, most preferably more than 6. The EPA, HPA, DPA and DHA may be composed as a glyceride (such as triglyceride), an ester (such as ethyl ester), or a free fatty acid.

Example 31

The following is an example of an embodiment of the present invention.

| COMPOSITION 3 | | | |
|---|---|---|---|
| Composition | Minimum (mg/g) | Maximum (mg/g) | Target (mg/g) |
| Docosapentaenoic acid (DPA n-3) | 800 | 990 | 920 |

The DPA may be composed as a glyceride (such as triglyceride), an ester (such as ethyl ester), or a free fatty acid.

Example 32

A mixture of DPA and EPA was prepared by combining 1 g DPA Ethyl Ester (SE-133-III) with 10 g EPA Ethyl Ester, 914 mg/g (KD Pharma FM13001) in 150 ml of 95% ethanol/water containing 35 ml of 2M sodium hydroxide. This reaction mixture was stirred overnight at ambient temperature. Tlc analysis showed complete conversion of the ethyl esters to the corresponding acids. The reaction mixture was cooled in an ice bath, acidified with 6N hydrochloric acid and concentrated on a rotavap under reduced pressure. Water and ethyl acetate were added, the phases separated and the aqueous residue extracted with ethyl acetate. The ethyl acetate extracts were combined, dried over sodium sulfate and concentrated to dryness on a rotavap under reduced pressure. Yield: 9.83 g. The ethyl ester mixture was then converted to the free fatty acids as described in example 7.

A representative sample of this ethyl ester composition was analysed using split inject by capillary gas chromatography by a 30 meter×0.25 mm Restek Stabil wax column using temperature programming.

Example 33

The following describes a study to determine the effect of compositions of the present invention.

STUDY #1—Zucker Rats

A DPA testing batch containing roughly 87% DPA ethyl ester was used to study pharmacodynamic effects in the Charles River Zucker fa/fa non-diabetic rat (strain code 185), which is known to display characteristics of insulin resistance, glucose intolerance, hyperinsulineamia, obesity and dyslipidemia. Male, eight to nine week old animals were used, with eight rats (n=8) per group. At the initiation of daily dosing, all animals were placed on chow+0.5% cholesterol diet (D13022002: Research Diets, New Brunswick, N.J.). Corn oil was used as a diluent for the omega-3 compounds, and methylcellulose to prepare the statin (atorvastatin) for dosing. A separate group of animals receiving corn oil alone was used as the untreated control group. Animals received daily doses of respective solutions by oral gavage. The study was conducted in 2 phases. In the first phase, DPA solution was administered at 50 mg/kg, 200 mg/kg, 400 mg/kg, and 1000 mg/kg. Animals were dosed daily for 14 days. For reference, a rat dose of 400 mg/kg would be equivalent to a human daily dose of approximately 4 grams (as shown in Reagan-Shaw et al. "Dose translation from animal to human studies revisited," *FASEB J.* 22, 659-661 (2007), which is incorporated by reference in its entirety).

The second phase was initiated on day 15, with the group receiving DPA 400 mg/kg solution being co-administered statin at 10 mg/kg. Another group, previously dosed with corn oil vehicle, receive atorvastatin to serve as an appropriate control. This second phase consisted of 14 days of daily, oral administration.

Plasma total cholesterol, LDL, HDL, VLDL, triglycerides and NEFA (non-esterified free fatty acids) are measured in the fasting state on day 0, 7 and 14; and for those groups included in the second phase on days 21 and 28. Levels of lipid parameters are determined in a 96-well multiplexed system using standard clinical chemistry techniques. Non-HDL cholesterol is calculated by subtracting the HDL value from the total cholesterol value. In addition, for the groups included in the second phase, insulin levels are determined at day 28. FIG. 1 shows the fasting plasma lipid values after seven days of dosing. FIG. 2 shows the fasting plasma insulin levels after 28 days of administration.

Figure 3:
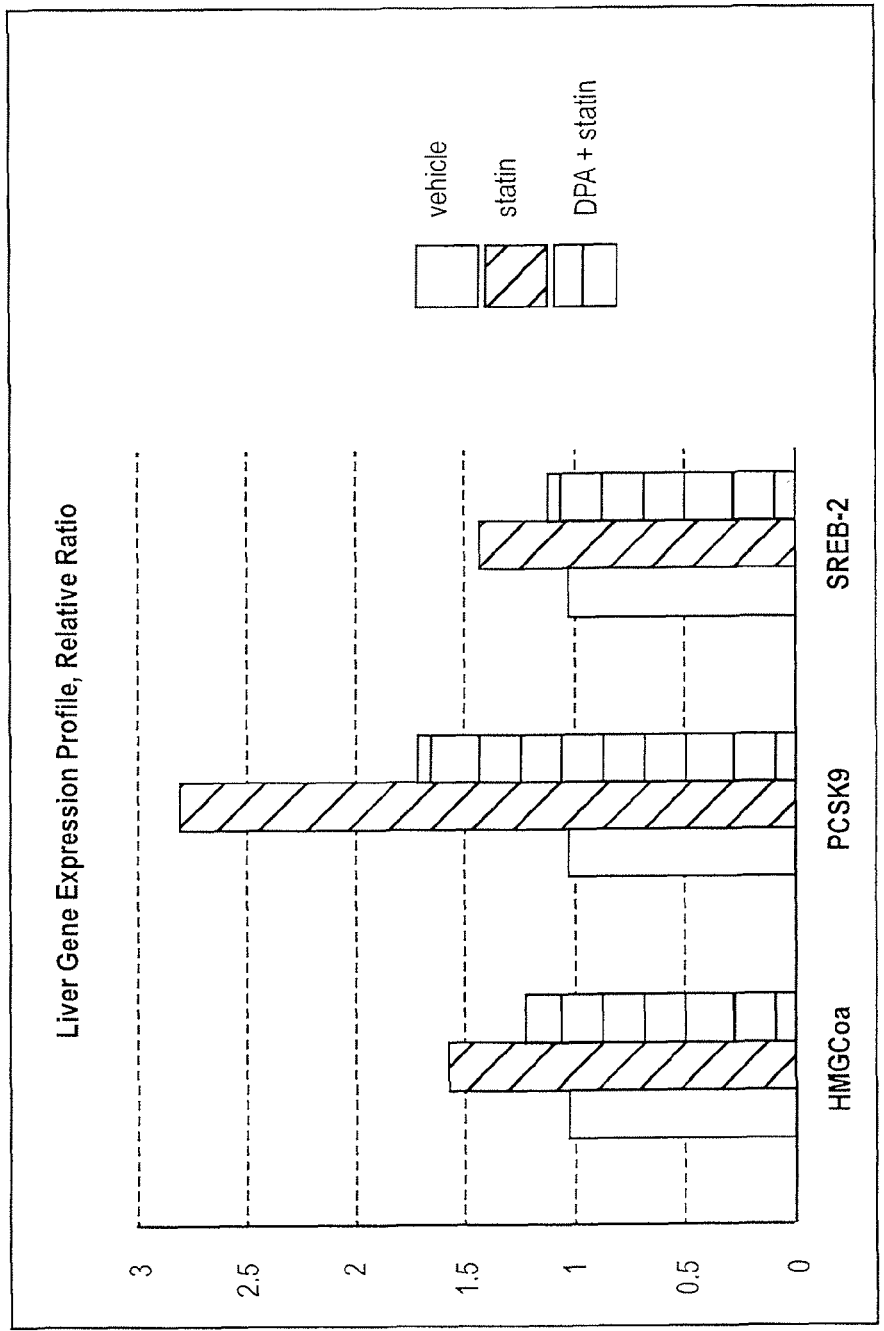
FIG. 3 shows the relative liver gene expression following 28 days of administration, relating to the study described in Example 33.

Expression of genes for HMGCoA (3-hydroxy-3-methyl-glutaryl-coenzyme A; key regulatory enzyme for new cholesterol biosynthesis), PCSK9 (pro-protein convertase subtilisin kexin 9; associated with LDL receptor functioning and increased levels of LDL), and SREB-2 (sterol regulatory enhancing binding protein 2; regulates transcription of a wide variety of genes involved with new cholesterol synthesis) are evaluated in liver from groups included in the second phase. The mRNA (messenger RNA) is isolated from samples previously frozen at −70° C.s, and cDNA (complementary DNA) is derived for further study using standard molecular biology technique. Samples and corresponding probes for genes of interest are loaded onto a Life Science TLDA card. The level of gene expression is quantified using real time RT-PCR (reverse transcriptase polymerase chain reaction) and calculated using the ΔΔCt technique relative to the vehicle group in accordance to methodology recommended and as described by Applied Biosystems (Guide to Performing Relative Quantitation of Gene Expression Using Real-Time Quantitative PCR). FIG. 3 shows the relative liver gene expression following 28 days of administration.

Example 34

The following describes a study to determine the effect of compositions of the present invention.

STUDY #2—Humans

The overall pharmacokinetics of one of COMPOSITION 1, 2 or 3 are evaluated versus a reference compound after administration under fasting or fed conditions in normal, mostly healthy volunteers in a standard, 4-way cross-over trial design format. VASCEPA®, EPANOVA™, LOVAZA®, or EPADEL® are used as a reference compound. A total of 48 subjects are separated into 2 groups of 24. Each subject serves as his or her own internal control for comparison purposes under this 4-way crossover design. Inclusion criteria for tested subjects include volunteers between ages 18-65, with a BMI of 30-35 (alternatively a BMI of 27-35) and triglyceride levels less than 350 mg/dL, who consume no more than 1 fish meal per week and who are not currently prescribed pharmaco-therapy for lowering triglycerides, including but not limited to fibrates, omega-3 agents, and niacin. Volunteers on stable anti-hypertensive, anti-diabetic and thyroid therapy re allowed for consideration. Any person on stable statin therapy is considered if their triglyceride levels are less than 350 mg/dL. However, the total composition of subjects in the study with this particular profile is limited to no more than 30%.

Volunteers self-administering omega-3 non-prescription dietary supplements are asked to refrain from their use 2 weeks prior to the initiation of the study until study completion.

Pharmacokinetic Study#2 Design

The effect of oral administration of the compounds tested in this study is evaluated under fed versus fasting administration conditions, in order to determine drug pharmacokinetics, as well as to understand the effects of food on drug pharmacokinetics. COMPOSITION 1 or the reference compound are dosed at approximately 4 grams/day in the morning by administration of 4 capsules containing approximately 1 gram of each compound. Several days prior to pharmacokinetic evaluations, volunteers are housed at the testing facility in order to ensure well-controlled experimental conditions.

Compounds are given to volunteers following an overnight fast, with plasma samples obtained prior to dosing and at various time points after day 1 and day 14 dosing. Volunteers are allowed access to water, and well-defined meals at certain times. Afterwards, compound administration is stopped for a 2-4 week washout period, and the groups are switched with respect to which compound they would receive, meaning that the group initially receiving COMPOSITION 1 is switched to receive the reference compound, and vice versa. Fasting pharmacokinetics are determined using the procedure described above. Following completion of the second 14-day dosing cycle, compound dosing is stopped for a 2-4-week washout period prior to the initiation of the a similar cycle as above, now with COMPOSITION 1 and the reference compound are administered together with a meal.

Plasma levels of omega-3 fatty acids of interest from the study are determined utilizing an analytical LC/MS technique under GLP laboratory conditions in order to determine Cmax, Tmax and AUC for the omega-3 fatty acids of interest, including EPA, DPA, HPA, DHA, and other omega-3 fatty acids.

Results

The results of the study show that COMPOSITION 1 has a better bioavalability (as measured by AUC and Cmax) than the reference compound. This effect is seen under fasting and/or fed administration conditions.

In an alternate study design, this Study #2 is conducted with a certain dose level of COMPOSITION 2 OR COMPOSITION 3 instead of COMPOSITION 1.

Example 35

The following describes a study (STUDY #3) to determine the effect of compositions of the present invention.

A Multi-Center, Placebo-Controlled, Randomized, Double-Blind, 12-Week Study to Evaluate the Efficacy and Safety of COMPOSITION 1, 2, or 3 in Patients With Fasting Triglyceride Levels ≥500 mg/dL and ≤2000 mg/dL:

This Phase 3, multi-center study consists of a 6- to 8-week screening/washout period (to include a diet and lifestyle stabilization period), which includes a fasting triglyceride (TG) qualifying period of 2-3 weeks, followed by a 12-week double-blind treatment period. Patients on statin therapy (with or without ezetimibe) at screening are evaluated by the investigator as to whether this therapy could be safely discontinued at screening, or if it is to be continued. Patients on any other dyslipidemia therapy need to discontinue these in order to qualify for the study. If statin therapy (with or without ezetimibe) is to be continued, dose(s) must be stable for weeks prior to the fasting TG baseline qualifying measurements for randomization. The screening visit is to occur at either 6 weeks before randomization for patients not on lipid-altering therapy at screening or for patients who do not need to discontinue their current dyslipidemia therapy, or at 8 weeks before randomization for patients who require washout of their current dyslipidemia therapy at screening.

The population for this study is men and women >18 years of age with a body mass index (BMI) ≤45 kg/m2. Patients on lipid-lowering therapy and patients not on lipid-lowering therapy are eligible to enroll in the study. Patients had to have an average TG level ≥500 mg/dL and ≤2000 mg/dL during the screening period to be eligible for randomization.

After confirmation of qualifying fasting TG values, eligible patients will enter a 12-week randomized, double-blind treatment period. At Week 0, patients will be randomly assigned to 1 of the following treatment groups: COMPOSITION 1 (approximately 2 g daily), COMPOSITION 1 (approximately 3 g daily), COMPOSITION 1 (approximately 4 g daily), or placebo. The daily dose may be taken as either a single dose or distributed over two doses per day.

Approximately 80 patients per treatment group will be randomized in this study. Stratification will be by baseline fasting TG level (≤750 mg/dL or >750 mg/dL, gender, and the use of statin therapy at randomization. During the double-blind treatment period, patients return to the site at Week 4, Week 11, and Week 12 for efficacy and safety evaluations.

The primary objective of the study is to determine the efficacy of COMPOSITION 1 at a approximately 2 g daily dose, approximately 3 g daily dose and approximately 4 g daily dose, compared to placebo, in lowering fasting TG levels in patients with fasting TG levels ≥500 mg/dL and ≤2000 mg/dL The secondary and exploratory objectives of the study are as follows:

1. To determine the safety and tolerability of COMPOSITION 1 at approximately 2 g daily, approximately 3 g daily and approximately 4 g daily;

2. To determine the effect of COMPOSITION 1 on lipid profiles, including total cholesterol (TC), non-high-density lipoprotein cholesterol (non-HDL-C) low-density lipoprotein cholesterol (LDL-C), high-density lipoprotein cholesterol (HDL-C), and very low-density lipoprotein cholesterol (VLDL-C);

3. To determine the effect of COMPOSITION 1 on apolipoprotein A-I (apo A-I), apolipoprotein B (apo B), apo A-I/apo B ratio, lipoprotein(a) (Lp[a]), and lipoprotein-associated phospholipase A2 (Lp-PLA2);

4. To determine the effect of COMPOSITION 1 on low-density lipoprotein (LDL) particle number and size, on oxidized LDL and on C-reactive protein (CRP).

5. To determine the effect of COMPOSITION 1 on intracellular adhesion molecule-1 (ICAM-1) vascular cell adhesion molecule 1 (VCAM_1), interleleukin-1β (IL-1β), interleukin-2 (IL-2), interleukin-6 (IL-6), interleukin-8 (IL-8), interleukin-10 (IL-10), interleukin-12 (IL-12), interleukin-15 (IL-15), interleukin-18 (IL-18), tumor necrosis factor-alpha (TNF-α), tumor necrosis factor-beta (TNF-β) and plasminogen activator inhibitor-1 (PAI-1);

6. To determine the effects of COMPOSITION 1 on nuclear factor kappa-light-chain-enhancer of activated B cells (NF-κB), vitronectin receptor (αvβ3), glycoprotein IIb/IIIa (gpIIb/IIIa and other platelet and thrombogenic factors.

7. To determine the effects of COMPOSITION 1 on E-selectin, P-selectin, homocysteine, thromboxane B2 (TXB2), thromboxane A2 (TXA2), thromboxane B23 (TXB3), thromboxane A3 (TXA3), 2,3-dinor thromboxane B2, free fatty acids (FFA or NEFA), serum amyloid A1, serum amyloid A2, serum amyloid A3, serum amyloid A4, thiobarbituric acid (TBA) reacting material, adiponectin (GBP-28), hemoglobin A1c (HbA1c), fasting insulin, fasting glucagon, fasting plasma glucose, fasting plasma fructosamine, macrophage colony stimulating factor (M-CSF) and granulocyte macrophage colony stimulating factor (GM-CSF).

8. To determine the effects of COMPOSITION 1 on fibrinogen, fibrin D-dimer, platelet derived-microparticles, mean platelet volume (MPV), platelet subpopulations, adenosine diphosphate induced platelet aggregation, platelet endothelial cell adhesion molecule (PECAM-1), heart rate, and systolic and diastolic blood pressure.

9. To investigate the relationship between changes in fatty acid concentrations (including EPA, DHA and DPA) in plasma and red blood cell membranes and the reduction in fasting TG levels;

10. To investigate the relationship between changes in fatty acid concentrations (including EPA, DHA and DPA) in plasma and red blood cell membranes and the reduction in fasting TG levels.

The primary efficacy variable for the double-blind treatment period is percent change in fasting TG from baseline to the Week 12 endpoint.

The secondary efficacy variable for the double-blind treatment period includes the following: Percent changes in fasting Non-HDL-C, LDL-C, VLDL-C, HDL-C, Lp-PLA2, and apo B from baseline to Week 12 endpoint.

Statistical methods for efficacy evaluations will be conducted on the intent-to-treat (ITT) and on the per-protocol population. Descriptive statistics for the baseline and post-baseline measurements, the percent changes, or changes from baseline are to be presented by treatment group and by visit for all efficacy variables.

The primary and secondary efficacy analyses will be performed using an analysis of covariance (ANCOVA) model with treatment, gender, and the use of statin therapy at randomization as factors and baseline fasting TG value as a covariate.

In an alternate study design, this Study #3 is conducted with one or more dose levels of COMPOSITION 2 OR 3 instead of COMPOSITION 1.

Example 36

The following describes a study (STUDY #4) to determine the effect of compositions of the present invention.

A Multi-Center, Placebo-Controlled, Randomized, Double-Blind, 6- to 12-Week Study to Evaluate the Efficacy and Safety of COMPOSITION 1, 2 or 3 in Statin-Treated Patients With High Fasting Triglyceride Levels ≥200 mg/dL and ≤499 mg/dL.

This multi-center study consists of a 4- to 6-week screening and washout period (to include a diet and lifestyle stabilization period, and to wash-out any non-statin/ezetimibe dyslipidemia medications), which also includes a 2-3 week fasting triglyceride (TG) level qualifying period, followed by a 6- to 12-week double-blind treatment period. Patients on statin therapy (with or without ezetimibe) at screening are evaluated by the investigator as to whether this therapy does maintain low-density lipoprotein (LDL) levels of ≥40 mg/dl and <100 mg/dl. At screening, statin therapy (with or without ezetimibe) is to be initiated, in those patients who are not on statin therapy in order to achieve LDL levels of ≥40 mg/dl and <100 mg/dl. Dose(s) of statin therapy must be stable for ≥4 weeks prior to the TG baseline qualifying measurements for randomization.

The population for this study is men and women >18 years of age with a body mass index (BMI) ≤45 kg/m2. Patients on lipid-lowering therapy and patients not on lipid-lowering therapy are eligible to enroll in the study. Patients had to have an average fasting TG level ≥200 mg/dL and ≤499 mg/dL during the qualifying period to be eligible for randomization.

After confirmation of qualifying fasting TG values, eligible patients will enter a 6- to 12-week randomized, double-blind treatment period. At Week 0, patients will be randomly assigned to one of the following treatment groups: COMPOSITION 1 at an approximately 2 gram daily dose, COMPOSITION 1 at an approximately 3 gram daily dose, COMPOSITION 1 at an approximately 4 gram daily dose, or placebo. The daily dose may be taken as either a single dose or distributed over two doses per day.

Approximately 100 to 250 patients per treatment group will be randomized in this study. Stratification will be by gender. During the double-blind treatment period, patients will return to the site at Week 3 or 4, one week prior to the last week of randomized treatment period, and at the end or the randomized treatment period for efficacy and safety evaluations.

The primary objective of the study is to determine the efficacy of COMPOSITION 1 at approximately 2 grams daily, approximately 3 grams daily and approximately 4 grams daily, compared to placebo, in lowering fasting TG levels in statin-treated patients with fasting TG levels ≥200 mg/dL and ≤499 mg/dL.

The secondary and exploratory objectives of the study may include but are not limited to the following objectives:

1. To determine the safety and tolerability of COMPOSITION 1 at approximately 2 g daily, approximately 3 g daily and approximately 4 g daily;

2. To determine the effect of COMPOSITION 1 at on lipid profiles, including total cholesterol (TC), non-high-density lipoprotein cholesterol (non-HDL-C) low-density lipoprotein cholesterol (LDL-C), high-density lipoprotein cholesterol (HDL-C), and very low-density lipoprotein cholesterol (VLDL-C);

3. To determine the effect of COMPOSITION 1 on apolipoprotein A-I (apo A-I), apolipoprotein B (apo B), apo A-I/apo B ratio, lipoprotein(a) (Lp[a]), and lipoprotein-associated phospholipase A2 (Lp-PLA2);

4. To determine the effect of COMPOSITION 1 on low-density lipoprotein (LDL) particle number and size, on oxidized LDL, high-sensitivity C-reactive protein (HSCRP). and on C-reactive protein (CRP).

5. To determine the effect of COMPOSITION 1 on intracellular adhesion molecule-1 (ICAM-1), vascular cell adhesion molecule 1 (VCAM__1), interleleukin-1β (IL-1β), interleukin-2 (IL-2), interleukin-6 (IL-6), interleukin-8 (IL-8), interleukin-10 (IL-10), interleukin-12 (IL-12), interleukin-15 (IL-15), interleukin-18 (IL-18), tumor necrosis factor-alpha (TNF-α), tumor necrosis factor-beta (TNF-β) and plasminogen activator inhibitor-1 (PAI-1);

6. To determine the effects of COMPOSITION 1 on nuclear factor kappa-light-chain-enhancer of activated B cells (NF-κB), vitronectin receptor (αvβ3), glycoprotein IIb/IIIa (gpIIb/IIIa and other platelet and thrombogenic factors.

7. To determine the effects of COMPOSITION 1 on E-selectin, P-selectin, homocysteine, thromboxane B2 (TXB2), thromboxane A2 (TXA2), thromboxane B23 (TXB3), thromboxane A3 (TXA3), 2,3-dinor thromboxane B2, free fatty acids (FFA or NEFA), serum amyloid A1, serum amyloid A2, serum amyloid A3, serum amyloid A4, thiobarbituric acid (TBA) reacting material, adiponectin (GBP-28), hemoglobin A1c (HbA1c), fasting insulin, fasting glucagon, fasting plasma glucose, fasting plasma fructosamine, macrophage colony stimulating factor (M-CSF) and granulocyte macrophage colony stimulating factor (GM-CSF).

8. To determine the effects of COMPOSITION 1 on fibrinogen, fibrin D-dimer, platelet derived-microparticles, mean platelet volume (MPV), platelet subpopulations, adenosine diphosphate induced platelet aggregation, platelet endothelial cell adhesion molecule (PECAM-1), heart rate, and systolic and diastolic blood pressure.

9. To determine the effects of COMPOSITION 1 on fatty acid concentrations (including EPA, DHA and DPA) in plasma and red blood cell membranes;

10. To investigate the relationship between changes in fatty acid concentrations (including EPA, DHA and DPA) in plasma and red blood cell membranes and the reduction in fasting TG levels.

The primary efficacy variable for the double-blind treatment period is percent change in fasting TG from baseline to the Week 6 to 12 endpoint.

The secondary efficacy variable for the double-blind treatment period include but are not limited to the following: Percent changes in fasting Non-HDL-C, LDL-C, VLDL-C, HDL-C, Lp-PLA2, and apo B from baseline to Week 6 to 12 endpoint.

Statistical methods for efficacy evaluations will be conducted on the intent-to-treat (ITT) and on the per-protocol population. Descriptive statistics for the baseline and post-baseline measurements, the percent changes, or changes from baseline are to be presented by treatment group and by visit for all efficacy variables.

The primary and secondary efficacy analyses will be performed using an analysis of covariance (ANCOVA) model with treatment, gender, the type of statin therapy and diagnosis of diabetes at randomization as factors and baseline fasting TG value as a covariate.

In an alternate study design, this Study #4 is conducted with one or more dose levels of COMPOSITION 2 OR 3 instead of COMPOSITION 1. In an alternative study design, Study #4 is conducted, enrolling patients with a baseline triglyceride level of about 300 to 499 mg/dL or about 350 too 400 mg/dL, instead of 200 to 499 mg/dL.

Example 37

The following describes a study (STUDY #5) to determine the effect of compositions of the present invention.

The impact on fasting triglyceride levels and other pharmacodynamic endpoints of one of COMPOSITION 1, 2 or 3 are evaluated versus a reference compound after administration under fasting or fed conditions in normal, mostly healthy volunteers in a standard, 4-way cross-over trial design format. VASCEPA®, EPANOVA™, LOVAZA®, or EPADEL® are used as a reference compound. A total of 48 subjects are separated into 2 groups of 24. Each subject serves as his or her own internal control for comparison purposes under this 4-way crossover design. Inclusion criteria for tested subjects include volunteers between ages 18-65, with a BMI of 30-35 (alternatively a BMI of 27-35) and triglyceride levels less than 350 mg/dL, who consume no more than 1 fish meal per week and who are not currently prescribed pharmaco-therapy for lowering triglycerides, including but not limited to fibrates, omega-3 agents, and niacin. Volunteers on stable anti-hypertensive, anti-diabetic and thyroid therapy re allowed for consideration. Any person on stable statin therapy is considered if his or her triglyceride levels are less than 350 mg/dL. However, the total composition of subjects in the study with this particular profile is limited to no more than 30%.

Volunteers self-administering omega-3 non-prescription dietary supplements are asked to refrain from their use 2 weeks prior to the initiation of the study until study completion. Subjects using any other non-steroidal anti-inflammatory agents other than acetaminophen are asked to abstain and switch to acetaminophen for relief of pain, or are excluded from study consideration. Subjects are excluded if they receive any type of hormone therapy, weight loss agents, HIV therapy, beta-blockers, or are diagnosed with known cardiovascular disease, including heart failure, arrhythmia, any incidence of acute coronary syndrome, myocardial infarct, coronary artery bypass graft surgery, and/or angioplasty.

STUDY #5 Design

The effect of oral administration of the compounds tested in this study is evaluated under fed versus fasting administration conditions, in order to determine drug pharmacodynamics and effects on lipids. COMPOSITION 1 or the reference compound are dosed at approximately 4 grams/day in the morning by administration of 4 capsules containing 1 gram of each compound.

Compounds are given to volunteers following an overnight fast, with plasma samples obtained prior to dosing on day 1 and day 14 dosing. Volunteers are allowed access to water, and well-defined meals at certain times. Afterwards, compound administration is stopped for a 2-4 week washout period, and the groups are switched with respect to which compound they would receive, meaning that the group initially receiving COMPOSITION 1 is switched to receive the reference compound, and vice versa. Following completion of the second 14-day dosing cycle, compound dosing is stopped for a 2-4-week washout period prior to the initiation of the a similar cycle as above, now with COMPOSITION 1 and the reference compound are administered together with a meal.

Baseline plasma levels of fasting serum triglycerides are determined on day 1 and just prior to initiation and completion of either the fasting or fed multi-dosing period. Additional lipid and other parameters (see below under "Results") that are analyzed included total cholesterol, LDL, HDL, VLDL, non-HDL, and NEFA as previously described.

Effects on platelet function, such as clotting time and PAF-induced aggregation are also determined. Standard physiological, plasma and urinary safety markers, including but not limited to electrolytes, ALT, AST, BUN, glucose, blood pressure, weight etc. are monitored in accordance with standard good clinical trial guidelines.

Results

The results of the study show that COMPOSITION 1 has a better fasting triglyceride lowering effect than the reference compound. This effect is seen under fasting and/or fed administration conditions. Administration of COMPOSITION 1 have a beneficial effect, versus baseline and versus the reference compound, on other lipid parameters (such as HDL cholesterol, total cholesterol, non-HDL cholesterol, VLDL cholesterol), on platelet function, and one or more of the following: apolipoprotein A-I (apo A-I), apolipoprotein B (apo B), apo A-I/apo B ratio, lipoprotein(a) (Lp[a]), lipoprotein-associated phospholipase A2 (Lp-PLA2), low density lipoprotein (LDL) particle number and size, oxidized LDL, C-reactive protein (CRP), high sensitivity C-reactive protein (HSCRP), intracellular adhesion molecule-1 (ICAM-1), E-selectin, P-selectin, vascular cell adhesion molecule 1 (VCAM-1) or cluster of differentiation 106 (CD106), interleukin-1β (IL-1β), interleukin-2 (IL-2), interleukin-6 (IL-6), interleukin-8 (IL-8), interleukin-10 (IL-10), interleukin-12 (IL-12), interleukin-15 (IL-15), interleukin-18 (IL-18), tumor necrosis factor-alpha (TNF-α), tumor necrosis factor-beta (TNF-β), plasminogen activator inhibitor-1 (PAI-1), homocysteine, thromboxane B2 (TXB2), thromboxane A2 (TXA2), 2,3-dinor thromboxane B2, free fatty acids (FFA), serum amyloid A1, serum amyloid A2, serum amyloid A3, serum amyloid A4, thiobarbituric acid (TBA) reacting material, adiponectin (GBP-28), hemoglobin A1c (HbA1c), macrophage colony stimulating factor (M-CSF), granulocyte macrophage colony stimulating factor (GM-CSF), fibrinogen, fibrin D-dimer, platelet derived-microparticles, mean platelet volume (MPV), platelet subpopulations, heart rate, systolic and diastolic blood pressure, nuclear factor kappa-light-chain enhancer of activated B cells (NF-κβ), adenosine diphosphate induced platelet aggregation, platelet endothelial cell adhesion molecule (PECAM-1), vitronectin receptor ($\alpha_v\beta_v$), and glycoprotein IIb/IIIa (gpIIb/IIIa). This effect is more beneficial than that observed with VASCEPA®. Administration of COMPOSITION 1 has a beneficial impact, or a minimal impact, or no impact, on other non-HDL lipid parameters, such as LDL cholesterol versus baseline and the reference compound. In an alternate study design, this Study #5 is conducted with a certain dose level of COMPOSITION 2 OR COMPOSITION 3 instead of COMPOSITION 1.

DESCRIPTION OF THE PREFERRED EMBODIMENTS

1. A fatty acid composition comprising at least 50% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
2. A fatty acid composition comprising at least 60% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
3. A fatty acid composition comprising at least 70% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
4. A fatty acid composition comprising at least 75% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
5. A fatty acid composition comprising at least 80% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
6. A fatty acid composition comprising at least 85% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
7. A fatty acid composition comprising at least 90% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
8. A fatty acid composition comprising at least 95% omega-3-fatty acids, salts or derivatives thereof, while comprising eicosapentaenoic acid (EPA; C20:5-n3) and docosapentaenoic acid (DPA; C22:5-n3) and wherein the EPA:DHA ratio is higher than 20:1.
9. A composition according to one of the preferred embodiments 1 through 8, comprising at least 2% docosapentaenoic acid (DPA; C22:5-n3).
10. A composition according to one of the preferred embodiments 1 through 8, comprising at least 4% docosapentaenoic acid (DPA; C22:5-n3).
11. A composition according to one of the preferred embodiments 1 through 8, comprising at least 5% docosapentaenoic acid (DPA; C22:5-n3).
12. A composition according to one of the preferred embodiments 1 through 8, comprising at least 6% docosapentaenoic acid (DPA; C22:5-n3).
13. A composition according to one of the preferred embodiments 1 through 8, comprising at least 7% docosapentaenoic acid (DPA; C22:5-n3).
14. A composition according to one of the preferred embodiments 1 through 8, comprising at least 8% docosapentaenoic acid (DPA; C22:5-n3).
15. A composition according to one of the preferred embodiments 1 through 8, comprising at least 10% docosapentaenoic acid (DPA; C22:5-n3).
16. A composition according to one of the preferred embodiments 1 through 8, comprising at least 12% docosapentaenoic acid (DPA; C22:5-n3).
17. A composition according to one of the preferred embodiments 1 through 8, comprising at least 15% docosapentaenoic acid (DPA; C22:5-n3).
18. A composition according to one of the preferred embodiments 1 through 17, comprising no more than 95% EPA.
19. A composition according to one of the preferred embodiments 1 through 17, comprising no more than 10% omega-6 fatty acids.
20. A composition according to one of the preferred embodiments 1 through 17, comprising no more than 7% omega-6 fatty acids.
21. A composition according to one of the preferred embodiments 1 through 17, comprising no more than 5% omega-6 fatty acids.
22. A composition according to one of the preferred embodiments 1 through 17, comprising no more than 3% omega-6 fatty acids.
23. A composition according to one of the preferred embodiments 1 through 22, comprising no more than 5% arachidonic acid (C22:4-n6).
24. A composition according to one of the preferred embodiments 1 through 22, comprising no more than 4% arachidonic acid (C22:4-n6).
25. A composition according to one of the preferred embodiments 1 through 22, comprising no more than 3% arachidonic acid (C22:4-n6).
26. A composition according to one of the preferred embodiments 1 through 22, comprising no more than 2% arachidonic acid (C22:4-n6).
27. A composition according to one of the preferred embodiments 1 through 22, comprising no more than 1% arachidonic acid (C22:4-n6).
28. A composition according to one of the preferred embodiments 1 through 27, also comprising heneicosapentaenoic acid (C21:5-n3).
29. A composition according to one of the preferred embodiments 1 through 27, comprising at least 0.01% heneicosapentaenoic acid (C21:5-n3).
30. A composition according to one of the preferred embodiments 1 through 27, comprising at least 0.1% heneicosapentaenoic acid (C21:5-n3).
31. A composition according to one of the preferred embodiments 1 through 27, comprising at least 0.3% heneicosapentaenoic acid (C21:5-n3).
32. A composition according to one of the preferred embodiments 1 through 27, comprising at least 0.5% heneicosapentaenoic acid (C21:5-n3).
33. A composition according to one of the preferred embodiments 1 through 27, comprising at least 1% heneicosapentaenoic acid (C21:5-n3).
34. A composition according to one of the preferred embodiments 1 through 27, comprising at least 2% heneicosapentaenoic acid (C21:5-n3).
35. A composition according to one of the preferred embodiments 1 through 27, comprising at least 3% heneicosapentaenoic acid (C21:5-n3).
36. A composition according to one of the preferred embodiments 1 through 27, comprising at least 4% heneicosapentaenoic acid (C21:5-n3).
37. A composition according to one of the preferred embodiments 1 through 27, comprising at least 5% heneicosapentaenoic acid (C21:5-n3).
38. A composition according to one of the preferred embodiments 1 through 37, comprising no more than 5% omega-3 fatty acids that are not omega-3-pentaenoic acids.

39. A composition according to one of the preferred embodiments 1 through 37, comprising no more than 4% omega-3 fatty acids that are not omega-3-pentaenoic acids.
40. A composition according to one of the preferred embodiments 1 through 37, comprising no more than 3% omega-3 fatty acids that are not omega-3-pentaenoic acids.
41. A composition according to one of the preferred embodiments 1 through 37, comprising no more than 2% omega-3 fatty acids that are not omega-3-pentaenoic acids.
42. A composition according to one of the preferred embodiments 1 through 37, comprising no more than 1.5% omega-3 fatty acids that are not omega-3-pentaenoic acids.
43. A composition according to one of the preferred embodiments 1 through 37, comprising no more than 1.25% omega-3 fatty acids that are not omega-3-pentaenoic acids.
44. A composition according to one of the preferred embodiments 1 through 37, comprising no more than 1% omega-3 fatty acids that are not omega-3-pentaenoic acids.
45. A composition according to one of the preferred embodiments 1 through 44, wherein the EPA:DPA ratio is between 99:1 and 1:99.
46. A composition according to one of the preferred embodiments 1 through 44, wherein the EPA:DPA ratio is between 60:1 and 1:60.
47. A composition according to one of the preferred embodiments 1 through 44, wherein the EPA:DPA ratio is between 50:1 and 1:10.
48. A composition according to one of the preferred embodiments 1 through 44, wherein the EPA:DPA ratio is between 40:1 and 1:3.
49. A composition according to one of the preferred embodiments 1 through 44, wherein the EPA:DPA ratio is between 40:1 and 1:2.
50. A composition according to one of the preferred embodiments 1 through 44, wherein the EPA:DPA ratio is between 40:1 and 1:1.
51. A composition according to one of the preferred embodiments 1 through 44, wherein the EPA:DPA ratio is between 30:1 and 1:1.
52. A composition according to one of the preferred embodiments 1 through 44, wherein the EPA:DPA ratio is between 20:1 and 1:1.
53. A composition according to one of the preferred embodiments 1 through 44, wherein the EPA:DPA ratio is between 10:1 and 1:1.
54. A composition according to one of the preferred embodiments 1 through 44, wherein the EPA:DPA ratio is between 5:1 and 1:1.
55. A composition according to one of the preferred embodiments 1 through 44, wherein the EPA:DPA ratio is between 10:1 and 2:1.
56. A composition according to one of the preferred embodiments 1 through 44, wherein the EPA:DPA ratio is between 20:1 and 2:1.
57. A composition according to one of the preferred embodiments 1 through 44, wherein the EPA:DPA ratio is between 30:1 and 2:1.
58. A composition according to one of the preferred embodiments 1 through 44, wherein the EPA:DPA ratio is between 40:1 and 2:1.
59. A composition according to one of the preferred embodiments 1 through 44, wherein the EPA:DPA ratio is between 50:1 and 2:1.
60. A composition according to one of the preferred embodiments 1 through 44, wherein the EPA:DPA ratio is between 10:1 and 3:1.
61. A composition according to one of the preferred embodiments 1 through 44, wherein the EPA:DPA ratio is between 20:1 and 3:1.
62. A composition according to one of the preferred embodiments 1 through 44, wherein the EPA:DPA ratio is between 30:1 and 3:1.
63. A composition according to one of the preferred embodiments 1 through 44, wherein the EPA:DPA ratio is between 40:1 and 3:1.
64. A composition according to one of the preferred embodiments 1 through 44, wherein the EPA:DPA ratio is between 50:1 and 3:1.
65. A composition according to one of the preferred embodiments 1 through 44, wherein the EPA:DPA ratio is between 60:1 and 3:1.
66. A composition according to one of the preferred embodiments 1 through 44, wherein the EPA:DPA ratio is between 10:1 and 5:1.
67. A composition according to one of the preferred embodiments 1 through 44, wherein the EPA:DPA ratio is between 20:1 and 5:1.
68. A composition according to one of the preferred embodiments 1 through 44, wherein the EPA:DPA ratio is between 30:1 and 5:1.
69. A composition according to one of the preferred embodiments 1 through 44, wherein the EPA:DPA ratio is between 40:1 and 5:1.
70. A composition according to one of the preferred embodiments 1 through 44, wherein the EPA:DPA ratio is between 50:1 and 5:1.
71. A composition according to one of the preferred embodiments 1 through 44, wherein the EPA:DPA ratio is between 60:1 and 5:1.
72. A composition according to one of the preferred embodiments 1 through 44, wherein the EPA:DPA ratio is between 20:1 and 10:1.
73. A composition according to one of the preferred embodiments 1 through 44, wherein the EPA:DPA ratio is between 30:1 and 10:1.
74. A composition according to one of the preferred embodiments 1 through 44, wherein the EPA:DPA ratio is between 40:1 and 10:1.
75. A composition according to one of the preferred embodiments 1 through 44, wherein the EPA:DPA ratio is between 50:1 and 10:1.
76. A composition according to one of the preferred embodiments 1 through 44, wherein the EPA:DPA ratio is between 60:1 and 10:1.
77. A composition according to one of the preferred embodiments 1 through 44, wherein the EPA:DPA ratio is between 100:1 and 10:1.
78. A composition according to one of the preferred embodiments 1 through 44, comprising between 55% and 95% EPA.
79. A composition according to one of the preferred embodiments 1 through 44, comprising between 60% and 95% EPA.
80. A composition according to one of the preferred embodiments 1 through 44, comprising between 65% and 95% EPA.
81. A composition according to one of the preferred embodiments 1 through 44, comprising between 70% and 95% EPA.
82. A composition according to one of the preferred embodiments 1 through 44, comprising between 75% and 95% EPA.

83. A composition according to one of the preferred embodiments 1 through 44, comprising between 80% and 95% EPA.
84. A composition according to one of the preferred embodiments 1 through 44, comprising between 85% and 95% EPA.
85. A composition according to one of the preferred embodiments 1 through 44, comprising between 90% and 95% EPA.
86. A composition according to one of the preferred embodiments 1 through 44, comprising between 1% and 3% DPA.
87. A composition according to one of the preferred embodiments 1 through 44, comprising between 1% and 5% DPA.
88. A composition according to one of the preferred embodiments 1 through 44, comprising between 2% and 10% DPA.
89. A composition according to one of the preferred embodiments 1 through 44, comprising between 3% and 20% DPA.
90. A composition according to one of the preferred embodiments 1 through 44, comprising between 3% and 30% DPA.
91. A composition according to one of the preferred embodiments 1 through 44, comprising between 3% and 50% DPA.
92. A composition according to one of the preferred embodiments 1 through 44, comprising between 3% and 75% DPA.
93. A composition according to one of the preferred embodiments 1 through 44, comprising between 3% and 90% DPA.
94. A fatty acid composition according to one of the preferred embodiments 1 through 93, in which the fatty acids are present as ethyl esters.
95. A fatty acid composition according to one of the preferred embodiments 1 through 93, in which the fatty acids are present as free fatty acids.
96. A fatty acid composition according to one of the preferred embodiments 1 through 93, in which the fatty acids are present as esters in di-glyceride form.
97. A fatty acid composition according to one of the preferred embodiments 1 through 93, in which the fatty acids are present as esters in triglyceride form.
98. A fatty acid composition according to one of the preferred embodiments 94 through 97, also comprising a suitable anti-oxidant in a concentration sufficient to protect the fatty acids of the composition from oxidation.
99. A pharmaceutically suitable formulation comprising one of the compositions according to preferred embodiments 94 through 98, in which the amount of eicosapentaenoic acid plus docosapentaenoic acid is present in an amount between 100 and 10,000 mg.
100. A pharmaceutically suitable formulation or dosage form comprising one of the compositions according to preferred embodiments 94 through 98, in which the amount of eicosapentaenoic acid plus docosapentaenoic acid is present in an amount between 250 and 1,250 mg.
101. A pharmaceutically suitable formulation or dosage form comprising one of the compositions according to preferred embodiments 94 through 98, in which the amount of eicosapentaenoic acid plus docosapentaenoic acid is present in an amount between 500 and 1,100 mg.
102. A pharmaceutically suitable formulation or dosage form comprising one of the compositions according to preferred embodiments 94 through 98, in which the amount of eicosapentaenoic acid plus docosapentaenoic acid is present in an amount between 100 and 10,000 mg.
103. A method of administration or treatment to a subject of a formulation or dosage form according to one of the preferred embodiments 94 through 102 at a daily dose between 100 and 10,000 mg.
104. A method of administration or treatment to a subject of a formulation or dosage form according to one of the preferred embodiments 94 through 102 at a daily dose between 500 and 5,000 mg.
105. A method of administration or treatment to a subject of a formulation or dosage form according to one of the preferred embodiments 94 through 102 at a daily dose between 1,500 and 4,100 mg.
106. A method of treatment according to preferred e embodiments 103 through 105, in which the subject is a patient diagnosed with very high triglycerides (equal or more than 500 mg/dL).
107. A method of treatment according to preferred embodiments 103 through 105, in which the subject is a patient diagnosed with high triglycerides (equal to or more than 200 mg/dL but less than 500 mg/dL).
108. A method of treatment according to preferred embodiments 103 through 105, in which the subject is a patient already undergoing treatment with a statin and then diagnosed with high triglycerides (equal to or more than 200 mg/dL but less than 500 mg/d L).
109. A method of treatment according to preferred embodiments 103 through 105, in which the subject is a patient diagnosed with mixed dyslipidemia with TG 200-499 mg/dL and LDL-cholesterol equal to or more than 190 mg/dL.
110. A method of treatment according to preferred embodiments 103 through 105, in which the subject is a patient diagnosed with mixed dyslipidemia with TG 300-700 mg/dL and LDL-cholesterol equal to or more than 190 mg/dL.
111. A method of treatment according to preferred embodiments 103 through 105, in which the subject is a patient diagnosed with mixed dyslipidemia with TG 200-499 mg/dL and non-HDL-cholesterol equal to or more than 200 mg/dL.
112. A method of treatment according to preferred embodiments 103 through 105, in which the subject is a patient diagnosed with mixed dyslipidemia with TG 300-700 mg/dL and non-HDL-cholesterol equal to or more than 200 mg/dL.
113. A method of treatment according to preferred embodiments 103 through 105, in which the subject is a patient diagnosed with mixed dyslipidemia with TG 200-499 mg/dL and LDL-cholesterol equal to or more than 160 mg/dL.
114. A method of treatment according to preferred embodiments 103 through 105, in which the subject is a patient diagnosed with mixed dyslipidemia with TG 300-700 mg/dL and LDL-cholesterol equal to or more than 160 mg/dL.
115. A method of treatment according to preferred embodiments 103 through 105, in which the subject is a patient diagnosed with mixed dyslipidemia with TG 200-499 mg/dL and non-HDL-cholesterol equal to or more than 160 mg/dL.
116. A method of treatment according to preferred embodiments 103 through 105, in which the subject is a patient diagnosed with mixed dyslipidemia with TG 300-700 mg/dL and non-HDL-cholesterol equal to or more than 160 mg/dL.
117. A method of treatment according to preferred embodiments 103 through 105, in which the subject is a patient diagnosed with mixed dyslipidemia with TG 200-499 mg/dL and LDL-cholesterol equal to or more than 130 mg/dL.
118. A method of treatment according to preferred embodiments 103 through 105, in which the subject is a patient diagnosed with mixed dyslipidemia with TG 300-700 mg/dL and LDL-cholesterol equal to or more than 130 mg/dL.
119. A method of treatment according to preferred embodiments 103 through 105, in which the subject is a patient diagnosed with mixed dyslipidemia with TG 200-499 mg/dL and non-HDL-cholesterol equal to or more than 130 mg/dL.
120. A method of treatment according to preferred embodiments 103 through 105, in which the subject is a patient diagnosed with mixed dyslipidemia with TG 300-700 mg/dL and non-HDL-cholesterol equal to or more than 130 mg/dL.
121. A method of treatment according to preferred embodiments 103 through 105, in which the subject is a patient diagnosed/assessed to be at substantially elevated risk for cardiovascular events.
122. A method of treatment according to preferred embodiments 103 through 105, in which the subject is a patient diagnosed with diabetes.
123. A method of treatment according to preferred embodiments 103 through 105, in which the subject is a patient diagnosed with pre-diabetes or metabolic syndrome.
124. A method of treatment according to one of the preferred embodiments 103 through 123, in which the treatment results in significant reduction of blood, serum or plasma triglyceride levels.
125. A method of treatment according to one of the preferred embodiments 103 through 123, in which the treatment results in significant reduction of blood, serum or plasma triglyceride levels while not significantly increasing blood, serum or plasma LDL-cholesterol levels.
126. A method of treatment according to one of the preferred embodiments 103 through 123, in which the treatment results in significant reduction of blood, serum or plasma total-cholesterol levels.
127. A method of treatment according to one of the preferred embodiments 103 through 123, in which the treatment results in significant reduction of blood, serum or plasma non-HDL-cholesterol levels.
128. A method of treatment according to one of the preferred embodiments 103 through 123, in which the treatment results in significant reduction of blood, serum or plasma LDL-cholesterol levels.
129. A method of treatment according to one of the preferred embodiments 103 through 123, in which the treatment results in significant reduction of blood, serum or plasma VLDL-cholesterol levels.
130. A method of treatment according to one of the preferred embodiments 103 through 123, in which the treatment results in significant reduction of blood, serum or plasma VLDL-cholesterol levels while not significantly increasing blood, serum or plasma LDL-cholesterol levels.
131. A method of treatment according to one of the preferred embodiments 103 through 123, in which the treatment results in significant reduction of blood, serum or plasma apo-B levels.
132. A method of treatment according to one of the preferred embodiments 103 through 123, in which the treatment results in significant reduction of blood, serum or plasma apo-C-III levels.
133. A method of treatment according to one of the preferred embodiments 103 through 123, in which the treatment results in significant reduction of blood, serum or plasma LP-PLA2 levels.
134. A method of treatment according to one of the preferred embodiments 103 through 123, in which the treatment results in significant reduction of blood, serum or plasma hs-CRP levels.
135. A method of treatment according to one of the preferred embodiments 103 through 123, in which the treatment results in significant increase of blood, serum or plasma HDL-cholesterol levels.
136. A method of treatment according to one of the preferred embodiments 103 through 123, in which the treatment results in significant increase of blood, serum or plasma apo-A levels.
137. A method of treatment according to one of the preferred embodiments 103 through 123, in which the treatment results in significant reduction of the risk of suffering certain cardiovascular events.

What is claimed:

1. A method of reducing triglyceride levels from a baseline triglyceride level in a human subject in need thereof, comprising administering to the human subject a composition comprising a daily dosage of omega-3 docosapentaenoic acid (DPA) of 160 mg/day to about 600 mg/day and optionally docosahexaenoic acid (DHA), wherein when DHA is present, the ratio of DHA:DPA is no more than 2:1.

2. The method of claim 1, wherein the composition comprises a daily dosage of DPA of 180 mg/day to 500 mg/day.

3. The method of claim 1, wherein the composition comprises a daily dosage of DPA of 160 mg/day to about 200 mg/day.

4. The method of claim 1, wherein the composition comprises a daily dosage of DPA of about 250 mg/day to about 300 mg/day.

5. The method of claim 1, wherein the composition comprises a daily dosage of DPA of about 300 mg/day to about 400 mg/day.

6. The method of claim 1, wherein the composition further comprises eicosapentaenoic acid (EPA) and, wherein the amount of EPA and DPA is about 55% or more by weight of the total amount of fatty acids, and optionally comprises docosahexaenoic acid (DHA), wherein when DHA is present, the ratio of DHA:DPA is no more than 1:1.

7. The method of claim 6, wherein the amount of EPA and DPA is selected from the group consisting of about 60% or more, about 65% or more, about 70% or more, about 75% or more, about 80% or more, about 85% or more, and about 90% or more by weight of the total amount of fatty acids.

8. The method of claim 1, wherein the composition further comprises omega-6 fatty acids in an amount of no more than 6% of total amount of fatty acids.

9. The method of claim 1, wherein the composition further comprises docosahexaenoic acid (DHA), and DHA is present in an amount of no more than about 30% by weight of fatty acids present in the composition.

10. The method of claim 1, wherein the composition further comprises docosahexaenoic acid (DHA), and DHA is present in an amount of no more than about 10% by weight of fatty acids present in the composition.

11. The method of claim 1, wherein the composition further comprises docosahexaenoic acid (DHA), and DHA is present in an amount of no more than about 5% by weight of fatty acids present in the composition.

12. The method of claim 1, wherein the composition comprises DPA in ethyl ester form.

13. The method of claim 1, wherein the composition comprises DPA in free fatty acid form.

14. The method of claim 1, wherein the composition further comprises docosahexaenoic acid (DHA), and the ratio of DHA:DPA is no more than 2:1.

15. The method of claim 1, wherein the composition further comprises docosahexaenoic acid (DHA), and the ratio of DHA:DPA is no more than 1:1.

16. The method of claim 1, wherein the composition further comprises docosahexaenoic acid (DHA), and the ratio of DHA:DPA is no more than 1:2.

17. The method of claim 1, wherein the composition further comprises docosahexaenoic acid (DHA), and the ratio of DHA:DPA is no more than 1:4.

18. The method of claim 1, wherein the composition comprises at least about 6% docosapentaenoic acid (DPA) by weight of fatty acids present in the composition.

19. The method of claim 1, wherein the composition comprises at least about 20% docosapentaenoic acid (DPA) by weight of fatty acids present in the composition.

20. The method of claim 1, wherein the composition comprises at least about 50% docosapentaenoic acid (DPA) by weight of fatty acids present in the composition.

21. The method of claim 1, wherein the composition further comprises eicosapentaenoic acid (EPA) and docosahexaenoic acid (DHA), wherein the amount of EPA and DPA is about 55% or more by weight of the total amount of fatty acids and the ratio of DHA:DPA is no more than 1:1.

* * * * *